US012714405B2

(12) United States Patent
Broger

(10) Patent No.: US 12,714,405 B2
(45) Date of Patent: Aug. 25, 2026

(54) DEVICE, SYSTEM AND METHOD FOR COLLECTING AND ELUTING AEROSOL PARTICLES FROM HUMAN BREATHS FOR ANALYSIS

(71) Applicant: Avelo AG, Schlieren (CH)

(72) Inventor: Tobias Broger, Schlieren (CH)

(73) Assignee: Avelo AG (CH)

(*) Notice: Subject to any disclaimer, the term of this patent is extended or adjusted under 35 U.S.C. 154(b) by 290 days.

(21) Appl. No.: 18/556,204

(22) PCT Filed: May 5, 2022

(86) PCT No.: PCT/EP2022/062209
§ 371 (c)(1),
(2) Date: Oct. 19, 2023

(87) PCT Pub. No.: WO2022/234044
PCT Pub. Date: Nov. 10, 2022

(65) Prior Publication Data

US 2024/0215961 A1 Jul. 4, 2024

Related U.S. Application Data

(60) Provisional application No. 63/184,407, filed on May 5, 2021.

(51) Int. Cl.
*A61B 10/00* (2006.01)
*A61B 5/08* (2006.01)
*A61B 5/097* (2006.01)

(52) U.S. Cl.
CPC .......... *A61B 10/0045* (2013.01); *A61B 5/082* (2013.01); *A61B 5/097* (2013.01);
(Continued)

(58) Field of Classification Search
CPC ......... A61B 5/082; A61B 5/097; A61B 10/00; A61B 10/0045; A61B 2560/0431
See application file for complete search history.

(56) References Cited

U.S. PATENT DOCUMENTS 10,591,460 B1 3/2020 Ahmad et al.
10,663,454 B2 5/2020 Godula-Jopek et al.
(Continued)

FOREIGN PATENT DOCUMENTS

WO 2021242907 A1 2/2021
WO 2021216386 A1 10/2021

OTHER PUBLICATIONS

European Patent Office; Search Report in related International Patent Application No. PCT/EP2022/062209 dated Oct. 11, 2022; 6 pages.

*Primary Examiner* — Chu Chuan Liu
(74) *Attorney, Agent, or Firm* — Dorton & Willis, LLP

(57) ABSTRACT

A device, system and method for collecting and eluting aerosol particles contained in a breath sample of a human or animal for the purpose of sampling non-volatile respiratory pathogens present in the breath sample. In at least some embodiments, the present invention provides such a device, system and method to collect, preserve, concentrate and release pathogen-specific biomarkers from breath aerosols for the subsequent analysis with immunoassays and molecular assays for the clinical diagnosis of respiratory tract infections in humans. The sampling device comprises an aqueous solution dissolvable polymer membrane installed in a housing of the sampling device in the flow path of the breath aerosol that sorbs the aerosol particles. The sampling device further comprises an engagement means for releasably engaging an elution device to the housing for introducing an aqueous solution into the housing and for dissolving
(Continued)

the polymer membrane upon contact with the aqueous solution.

18 Claims, 21 Drawing Sheets

(52) U.S. Cl.
CPC ................ *A61B 2010/0087* (2013.01); *A61B 2560/0431* (2013.01)

(56) References Cited

U.S. PATENT DOCUMENTS

| | | | | |
|---|---|---|---|---|
| 2005/0137491 | A1* | 6/2005 | Paz | A61B 5/0878 600/543 |
| 2012/0045752 | A1 | 2/2012 | Ensor et al. | |
| 2014/0366609 | A1* | 12/2014 | Beck | A61B 5/082 73/23.3 |
| 2015/0226726 | A1* | 8/2015 | Beck | A61B 5/082 73/23.3 |
| 2015/0377748 | A1 | 12/2015 | Cooper et al. | |
| 2016/0022946 | A1 | 1/2016 | Sislian et al. | |
| 2021/0059560 | A1 | 3/2021 | Allegra et al. | |
| 2022/0178922 | A1* | 6/2022 | Lampropoulos | A61B 10/00 |

* cited by examiner

500

Tidal breathing of a subject into the invented device
502

Bioaerosol containing pathogen biomarkers enter an aqueous liquid dissolable polymer material
504

Dissolution of the aqueous liquid dissolvable polymer in aqueous liquid from an over pressurized chamber
506

Detection of the pathogen biomarkers in a microfluidic assay
508

Transmission of the data to the data entry, processing and presentation unit
510

Calculation of a clinical prediction based on the pathogen data and clinical data entered by the user in an algorithm
512

Presentaion of the final result to the user
514

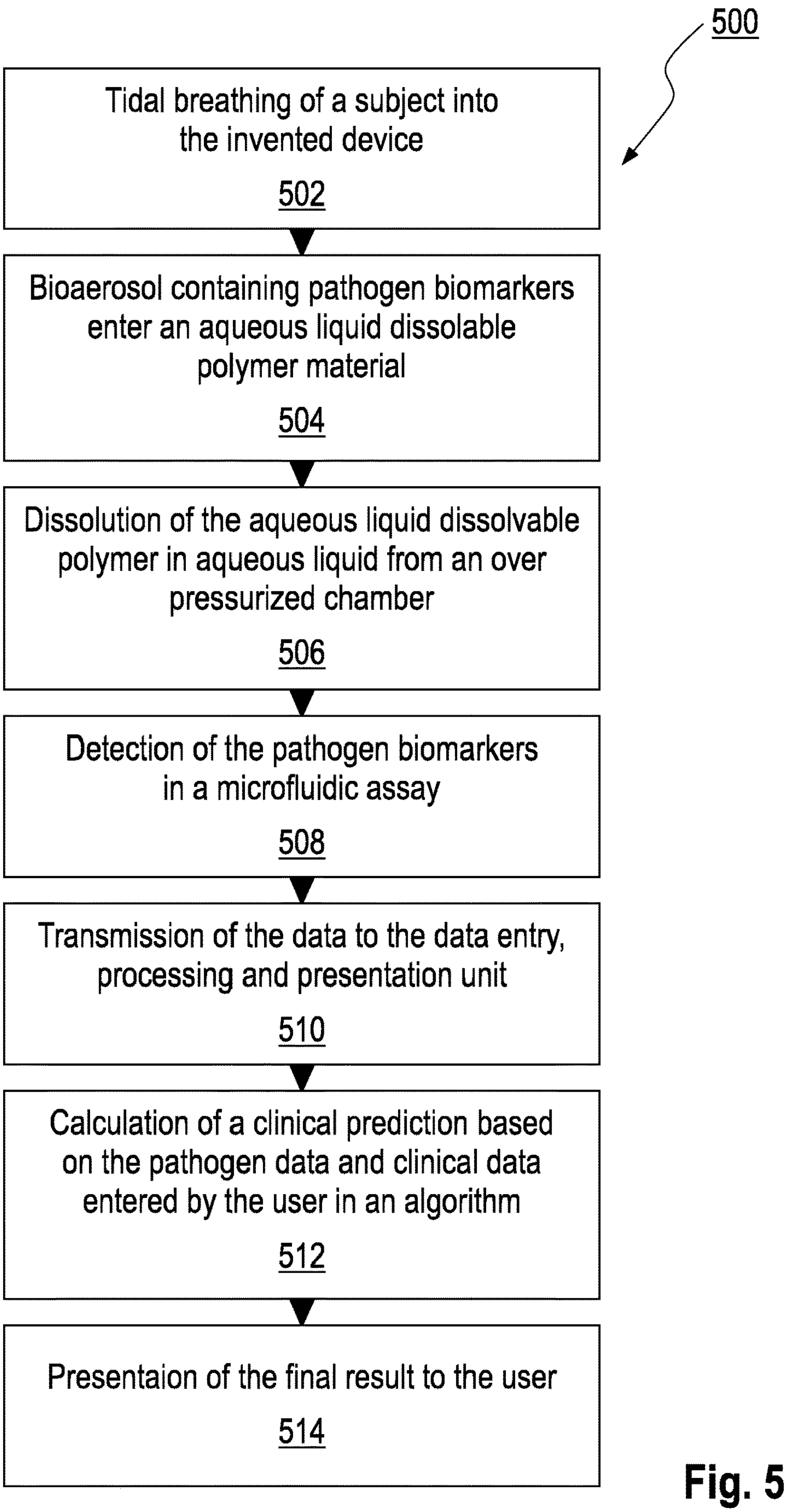

Fig. 5

916
1000
Medical User computational device (902A)
Detection device (936A)
Medical User computational device (902B)
Detection device (936B)
Server (920)
Electronic storage (922)
Processor(s) (930)
Memory (931)
Server app interface (932)
Analysis engine (934)
Patient computational device (1002)
Hospital computational device (1004)
Medical record computational device (1006)
Laboratory computational device (1008)

1301
1302
1303
1304
1305
1306
- dF/dT
1020
960
840
720
600
480
360
240
120
0
40.0
50.0
60.0
70.0
80.0
40.0
Temperature [°C]

Fig. 16
100
80
60
40
20
0
40 l/min
(female)
70 l/min
(female)
60 l/min
(male)
Exhaled air mass flow rate
in L/min
0
10
20
30
40
50
60
70
time in seconds

DEVICE, SYSTEM AND METHOD FOR COLLECTING AND ELUTING AEROSOL PARTICLES FROM HUMAN BREATHS FOR ANALYSIS

CROSS-REFERENCE TO RELATED APPLICATIONS

This application is a national phase application under 35 U.S.C. § 371 of International Patent Application No. PCT/EP2022/062209, filed May 5, 2022 (pending), which claims the benefit of priority to U.S. Provisional Patent Application No. 63/184,407, filed May 5, 2021, the disclosures of which are incorporated by reference herein in their entirety.

FIELD OF THE INVENTION

The present invention relates to a device, system and method for collecting aerosol particles contained in a breath sample of a human or animal for the purpose of sampling non-volatile respiratory pathogens present in the breath sample, and in particular to such a device, system and method for the improved collection, preservation, preparation, concentration and rapid release of pathogens and pathogen biomarkers for the subsequent analysis with immunoassays and molecular assays for the clinical diagnosis of respiratory tract infections.

BACKGROUND OF THE INVENTION

Up to 20% of all primary care consultations worldwide are due to respiratory infections. They result in 4 million deaths per year—almost all due to lower respiratory tract infections (LRTIs) causing pneumonia (Vos et al. Lancet 2020; 396(1082): 1204). On the one hand, bacterial infections require timely initiation of antibiotic treatment whereas, on the other hand, viral infections, such as influenza require treatment with antivirals if available.

Therefore, there is a strong need within the in-vitro diagnostics (IVD) industry to deliver improved rapid diagnostic solutions which detect respiratory tract infections in order to break the chain of transmission, initiate the right and timely treatment and avoid prescription of unnecessary antibiotics to fight antibiotic drug resistance. Rapid and simple sample collection and testing at the point-of-care where people first seek care and on easily available samples is needed. High priority target product profiles (TPP's) that describe the unmet diagnostic needs were developed by the World Health Organization (WHO) and other stakeholders and include (a) a TPP for a point-of-care test for community-acquired lower respiratory tract infection (Gal et al. PLOS One. 2018; 13 (8):e0200531) and (b) a TPP for a rapid non-sputum based test for detecting Tuberculosis (TB) (World Health Organization, High-priority target product profiles for new tuberculosis diagnostics: report of a consensus meeting, 2014 and Denkinger. JID. 2015; 211 (Suppl2)).

There are numerous prior art examples describing the use of swabs, sputum, saliva, and bronchoalveolar lavage (BAL) for the diagnosis of respiratory tract infections. These specimens limit the diagnosis of respiratory infectious diseases, particularly lower respiratory tract infections (LRTIs) as follows: (a) Nasopharyngeal or oropharyngeal swabs cause discomfort to the patient, require trained staff and miss LRTIs, (b) saliva and nasal swabs are potentially interesting for self-testing or at-home collection but contain no, or only low amounts of bacteria and viruses from the lower respiratory tract, limiting their use to diagnosis of upper respiratory tract infections, (c) sputum is the most common specimen for TB diagnosis but is difficult to obtain and the inhomogeneous sample matrix requires complex and costly sample preparation, (d) bronchoalveolar lavage (BAL) is the gold standard to diagnose LRTIs but requires special equipment (which is not available at the point-of-care), is highly invasive and may lead to complications. In sum, specimens from the upper respiratory tract might miss LRTIs and specimens from the lower respiratory tract are hard to obtain or require invasive procedures not feasible at the point-of-care.

To overcome these limitations of existing specimens, particularly in the diagnosis of lower respiratory tract infections, the use of breath samples from humans and/or animals is desirable.

There are numerous prior art examples that describe the collection and detection of volatile organic compounds (VOCs) in breath on sensor arrays such as electronic noses or mass spectrometry (U.S. Ser. No. 10/413,215, WO2017187141). However, the molecular entities of the detected VOCs and their origin are usually not defined and thus their relevance for a particular disease is unclear or even biologically implausible which led to low specificities, making VOC based systems inappropriate for clinical diagnosis. Further, mass spectrometers remain expensive, are relatively large instruments and therefore most likely not feasible for point-of-care use. Additionally, collected VOCs are not compatible with state-of-the art laboratory diagnostic methods such as polymerase chain reaction (PCR).

In contrast, it is well understood that human aerosols contain biologically plausible, nonvolatile pathogens, such as entire bacteria, virus, fungi and pathogen biomarkers such as nucleic acids (such as DNA and RNA) or pathogen antigens. Aerosols are a suspension of fine particles, particulate matter, "droplet nuclei" or liquid droplets (subsequently called "aerosol particles") in air. Physically speaking, an aerosol is a heterogeneous mixture of particles together with the gas or gas mixture surrounding them. Exhaled aerosol particles occur in multiple size modes that are associated with different generation sites and production mechanisms in the respiratory tract (Wang et al. Science. 2021; 373(6558)). Aerosol particles are typically ≤100 μm in diameter and may contain infectious bacteria and viruses and studies have shown that pathogens are enriched in small aerosol particles, typically ≤5 μm (Gralton et al. J Med Virol. 2013; 85(12):2151, Fennelly et al. Am J Respir Crit Care Med. 2004; 169(5):604). Aerosols that contain biological material such as cells like bacteria, or virus, biological molecules, by-products of metabolism and cell fragments are often referred to as bioaerosols which origin from a biological source or may affect a biological target. Many studies showed that respiratory infectious diseases including RSV (Kulkarni et al. Am J Respir Crit Care Med. 2016; 194(3):308), MERS-COV (Kim et al. Clin Infect Dis. 2016; 63(3):363), influenza (Yan et al. Proc Natl Acad Sci. 2018; 115(5):1081), and SARS-CoV-2 (Liu et al. Nature. 2020; 582(7813):557) are spread by particulates and aerosols (droplet and droplet nuclei) from coughing, sneezing, breathing, and talking. For Tuberculosis, the pioneering experiments of Riley and Wells (Am J Hyg. 1959; 70:185) more than 60 years ago proved airborne transmission by demonstrating that guinea pigs developed TB upon breathing air from remote ward housing TB patients. Since then, the presence of *Mycobacterium tuberculosis* (Mtb) and related biomarkers in aerosols has been well described in multiple research studies summarized by Fennelly et al. (Chest. 2020; 157(3):540).

Current sample collection and concentration devices for pathogen biomarkers from human breath aerosols have many desirable attributes but are inefficient and thus insufficiently sensitive and/or too complex with a high breathing resistance and/or do not teach a way for rapid and instrument-free elution of pathogen biomarkers. More efficient yet simpler collection of pathogen biomarkers from human breath to improve sensitivity with subsequent rapid elution of biomarkers for detection with diagnostic assays would clearly be desirable.

The background art fails to teach or suggest the reproducible collection and detection of biomarkers in aerosols. There are prior art examples that describe the collection of specific biomarkers in aerosols, all of which fail to meet medical standards. One of the limitations is the low sensitivity due to the low collection and concentration efficiency (EP 1 377 815). Another limitation is the insufficient, incomplete and time-consuming release of the collected specific biomarkers for subsequent detection (US 2020/0300876). Limitations of other, prior art examples for biological air and aerosol particles sampling are their requirement for active pumping which makes the instruments complex and unsuitable for human breath sampling with tidal breathing or exhalation where low breathing resistance is needed (US 2013/0273520). Further prior art examples do not describe an instrument-free combination of collection and elution.

WO 2012/024407 describes an aerosol collection system that uses a nanofiber mat with a plurality of electrospun nanofibers formed as a filter to collect aerosols. A pump is used to entrain air-borne particles in a gas stream.

WO 2013/132085 relates to a portable sampling device for aerosols. An electrostatic filter membrane is used to collect aerosols from exhaled breath of a subject. To filter out contaminants, such as saliva, mucus and large particles, baffle plates inside the sampling device are provided to obtain a non-straight gas flow through the device. After use, the device is sealed and then sent to a laboratory for further sensor based analysis.

U.S. Pat. No. 10,080,857 describes a system for breath sample collection and analysis. A subject exhales into a mouthpiece connected to a sample collector. The sample collector uses a nozzle and contains a liquid buffer downstream of the nozzle which collects the analyte. After use, the mouthpiece is disconnected, the sample collector is sealed and then transferred to a diagnostic device which analyses the analyte.

BRIEF SUMMARY OF THE INVENTION

It is an object of the present invention to eliminate, or at least mitigate the problems associated with prior art devices, systems and methods. In particular, it is an object of the present invention to not only improve the collection of non-volatile respiratory pathogens present in human or animal breath aerosol particles, but also the handling of the sample for the subsequent analysis with immunoassays and molecular assays for the clinical diagnosis of respiratory tract infections in humans.

These and other objects of the invention are solved by a device, system, and method for collection and eluting particles as shows and described herein.

The present invention relates to a device, system and method for collecting and eluting aerosol particles for analysis from a human person (subject). Although reference is made herein to "human breath", it is contemplated that the present invention would also be suitable for non-human animals. In addition, the present invention may also be used to collect particles from air in a room, for example, in which human beings gathered in order to test the air exhaled by the human beings for nonvolatile respiratory pathogens possibly present in the air.

In at least some embodiments, the present invention provides such a device, system and method to collect, preserve, concentrate and release pathogen-specific biomarkers from breath aerosol particles for the subsequent analysis with immunoassays and molecular assays for the clinical diagnosis of respiratory tract infections in humans. The sampling device comprises an aqueous solution dissolvable polymer material (subsequently called "polymer membrane") installed in the housing in the flow path of the human exhaled breath aerosol that sorbs and preserves aerosol particles that can be dissolved in an aqueous solution upon contact.

Non-limiting examples of suitable dissolvable polymer materials include polyvinyl alcohol (PVA), chitosan, polyethylene oxide (PEO), hydroxypropyl methylcellulose phthalate (HPMCP), and pullulan. The dissolvable polymer membrane may be provided in the form of a film or foil when used as impactors or as fibers or open-cellular foams or sponges when used as filters. Non-limiting examples for fiber production include electrospinning, melt blowing, blow spinning, wet spinning, direct drawing, centrifugal spinning, force spinning, touch- and brush-spinning, template synthesis, self-assembly, isolating fibers from plants or wood. In a preferred embodiment the dissolvable polymer membrane is an electrospun chitosan/polyethylene oxide (PEO) (mass ratio 8:2) fiber on an inert support mesh or PVA fibers electrospun on a PVA foil.

Without wishing to be limited by a single hypothesis, such a device provides a portable, hand-held, highly efficient, point-of-care collection and elution system for pathogen biomarkers like nucleic acids and antigens from human breath aerosol particles that is fully disposable and does not rely on complex instruments.

Furthermore, the elution is preferably done by connecting the sampling device to an elution device such as a tube containing an aqueous solution and turning it upside down to dissolve the polymer membrane as an effect of gravitational force. By way of example the aqueous solution is a stabilizing and/or inactivating transport buffer containing TRIS, ethylenediaminetetraacetic acid (EDTA), guanidine thiocyanate, guanidine hydrochloride, HEPES, Universal Transport Medium (UTM), liquid amies transport medium, Tween 20, Triton X100, tris(2-carboxyethyl)phosphine (TCEP), sodium chloride, phosphate-buffered saline, Hank's balanced salt solution, bovine serum albumin, L-cysteine, gelatin, sucrose, glutamic acid, vancomycin, amphotericin B, colistin, phenol red, sodium hydroxide, isopropanol or a combination thereof. This enables preservation of the breath aerosol sample containing the pathogens and pathogen biomarkers for the purpose of storage as well as safe shipment to centralized labs for subsequent clinical diagnosis of respiratory tract infections (e.g. with immunoassays and molecular assays). In one particular embodiment, the elution device is a standard clinical lab tube and therefore highly compatible with standard workflows of centralized labs. This not only speeds up the entire process from the point at which the aerosol sample is taken up to the point at which the sample undergoes clinical analysis, but also requires fewer logistic steps and minimizes the contamination risk of the biological sample. The immediate elution of the pathogen and pathogen biomarkers with a stabilizing aqueous solution right after the collection of the aerosol particles with the sampling device preserves the viability of the pathogen and stabilizes the pathogen biomarkers for transportation. In some embodiments, inactivation of the pathogen for safe transportation is desirable which can be achieved by an inactivating buffer that kills the pathogen but preserves the biomarkers. A non-limiting example is the use of guanidine thiocyanate containing buffer which inactivates the pathogen but preserves nucleic acids for transportation of the sample at ambient temperature. By way of example, the elution device containing the collected aerosol particles is shipped to a centralized laboratory for testing.

According to at least some embodiments, such a collection and elution system preferably includes relatively few parts for economical manufacturing. The sampling device preferably outputs a concentrated pathogen biomarker sample with compatibility with a variety of different assays, analyzers and methods for the detection of respiratory pathogens present anywhere in the respiratory tract, including without limitation the upper respiratory tract and/or the lower respiratory tract. Preferably the sampling device does not require powered equipment for collection and elution. Analyzers and assays used with the present invention can be point-of-care systems or centralized lab systems. Non-limiting examples of assays and detection methods include immunoassays, molecular assays including all nucleic acid amplification tests (NAATs such as PCR, isothermal amplification), DNA hybridization assays, CRISPR-based assays, sequencing assays, or growth assays.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit, including without limitation an ASIC (application-specific integrated circuit). As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Unless otherwise defined, all technical and scientific terms used herein have the same meaning as commonly understood by one of ordinary skill in the art to which this invention belongs. The materials, methods and examples provided herein are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 5 shows a flow-chart illustrating an exemplary method in accordance with the present disclosure.

DESCRIPTION OF AT LEAST SOME EMBODIMENTS

Figure 1:
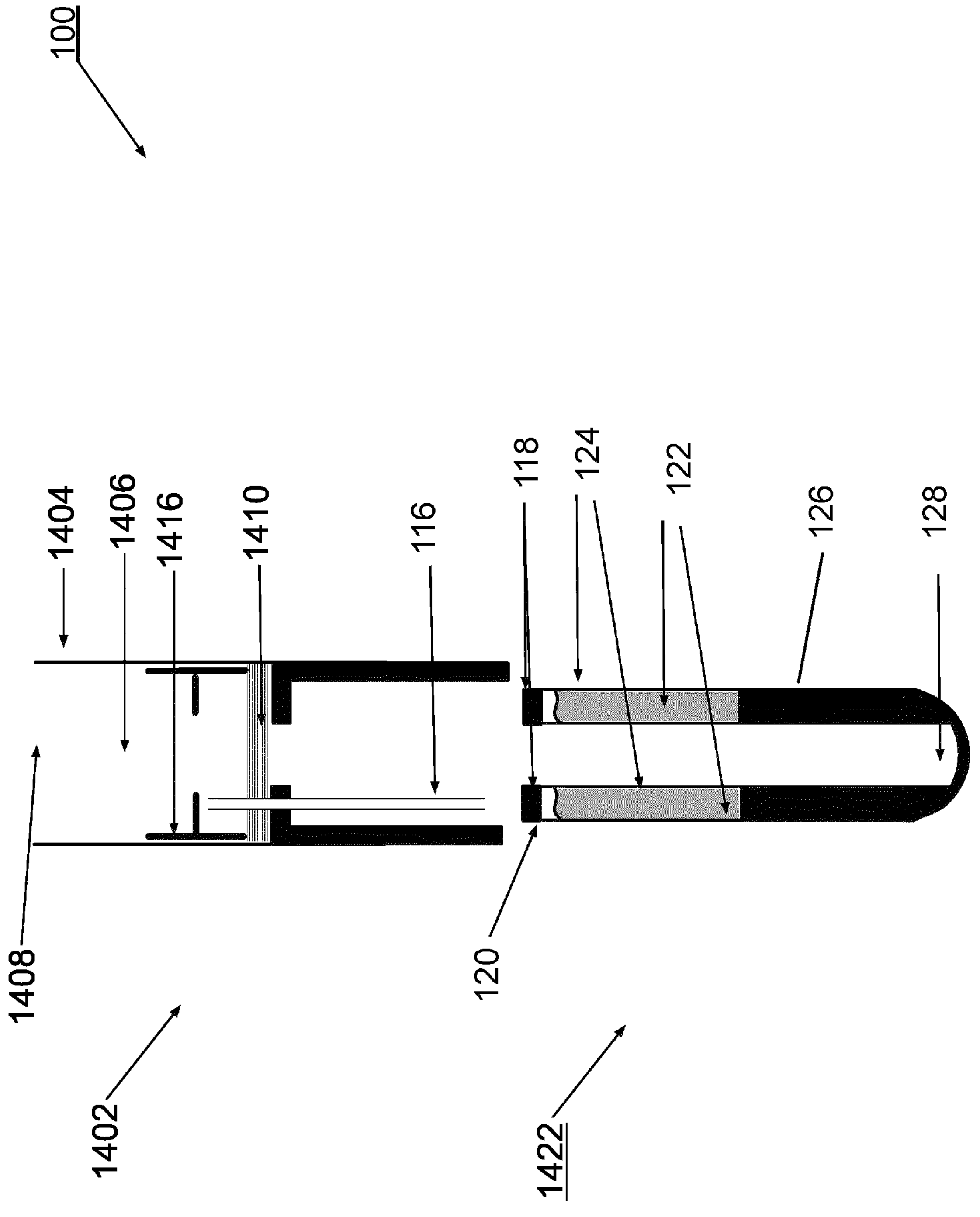
FIG. 1 is an exemplary, illustrative non-limiting diagrammatic side elevation view of the sampling device and the elution device of the present invention.

Specific examples of the disclosure will now be described with reference to the accompanying figures. Although specific configurations and arrangements are discussed, it should be understood that this is done for illustrative purposes only. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Some embodiments described herein relate to a breath aerosol particles sampling device and elution device in a microfluidic arrangement integrated within a microfluidic assay with a detection system for performing a variety of tests, such as immunoassays, isothermal amplification assay, PCR, DNA hybridization, sequencing etc. In an embodiment, the test cartridge integrates all of the components necessary to perform such tests into a single, disposable package. The test cartridge may be configured to be analyzed by an external detector to read the assay signal which has a connection to a data entry, data processing and presentation system which provides data related to the reactions that take place within the test cartridge. It optionally combines data from the detector with clinical data entered by the user in an algorithm, for example to determine the risk score for the subject for a particular respiratory disease such as pneumonia for example. It optionally then presents the final results to the user.

Although the description below refers to a sampling device, it may well be understood and therefore named as a collector, as it collects particles or particulate matter contained in a breath sample of a human or animal. At the time the particles or particulate matter are collected, they are only suspected to contain non-volatile respiratory pathogens. Tests carried out thereafter will provide qualitative positive or negative confirmation or quantification of the pathogen or pathogens. Hence, the sampling device serves the purpose to sample non-volatile respiratory pathogens possibly existing in the collected particles or particulate matter.

The description below also refers to an elution device that contains an aqueous solution suitable for dissolving a polymer membrane. It is conceivable that the polymer membrane is located on a substrate that is not dissolvable by the aqueous solution. Hence, the particles which originate from the aerosol and which are sorbed by the polymer membrane are washed out or eluted from the substrate by dissolution of the polymer membrane. Sorbtion by the polymer membrane may include adsorption and/or absorption and/or binding.

FIG. 1 is an exemplary, non-limiting diagrammatic side elevation view of the sampling device and the elution device of the present invention for the collection of molecules and/or structures and/or biomarkers related to respiratory pathogens. Without wishing to be limited by a single hypothesis, the sampling device is designed to collect such molecules and/or structures and/or biomarkers present in human breath aerosol particles prior to use.

As shown in a collector system 100, a sampling device 1402 comprises a tubular housing 1404 with an airflow path 1406 contained therein. Breath from a subject passes through a flow inlet 1408 in tubular housing 1404, through airflow path 1406, to a membrane 1410. Membrane 1410 preferably comprises a dissolvable polymer membrane which is held in position by a retainer element 1416. When breath passes through airflow path 1406, non-gaseous components of the breath are concentrated at membrane 1410. These non-gaseous components comprise solid and liquid particles and build an aerosol suspension together with the gaseous components. If a respiratory pathogen is present in the lungs, throat, mouth and/or other parts of the respiratory tract, molecules and/or structures and/or biomarkers from such a pathogen or the entire pathogen itself are expected to be present in the particles. Membrane 1410 preferably comprises a material through which such particles cannot pass, such that the particles become trapped and concentrated at membrane 1410. Without wishing to be limited by a single hypothesis, preferably membrane 1410 is configured to support collection of such particles in a sufficiently concentrated amount, without requiring excessive exhalation force on the part of the subject. Subjects having a reduced lung capacity, lung inflammation and/or otherwise unable to produce a great deal of force upon exhalation are able to provide a sufficient sample, due to the concentrating effect of membrane 1410.

A variety of dissolvable polymer materials are available and suitable for use for the polymer membrane 1410. Non-limiting examples of suitable dissolvable polymer materials include poly (vinyl alcohol) (PVA), chitosan, polyethylene oxide (PEO), hydroxypropyl methylcellulose phthalate (HPMCP), and pullulan. The dissolvable polymer membrane can be foils or films when used as impactors or fibers when used as filters or combinations thereof. In a preferred embodiment the dissolvable polymer membrane is an electrospun chitosan/polyethylene oxide (PEO) (mass ratio 8:2) nanofiber mat on an inert support mesh. In another preferred embodiment the dissolvable polymer membrane is a PVA fiber mat on a PVA foil.

To support elution of particles from polymer membrane 1410, preferably after the breath sample has been collected, optionally and preferably sampling device 1402 comprises an elution device 1422. Elution device 1422 may be placed in fluidic communication with sampling device 1402 after the breath sample is collected or may be in fluidic communication before the breath sample is collected. If elution device 1422 is placed in fluidic communication with sampling device 1402 after the breath sample is collected, then optionally a communication element 116 supports fluidic communication through polymer membrane 1410.

In this non-limiting example, the communication element comprises a needle 116, which punctures or breaches polymer membrane 1410, such that fluids (including without limitation liquids and/or gases) can pass through the puncture or breach from sampling device 1402 to elution device 1422.

When connecting the sampling device 1402 and the elution device 1422, preferably needle 116 pierces a septum 118. Septum 118 is preferably positioned at an upper end 120 of elution device 1422, close to the connection with sampling device 1402. Optionally placing upper end 120 in physical contact with sampling device 1402, for example with pressure, a rotation and/or other motion, causes septum 118 to be pierced, breached or other disruption. Such disruption of septum 118 permits an aqueous solution 122 to come in contact with polymer membrane 1410. Aqueous solution 122 may be provided in an overpressure chamber 124 as shown. Overpressure chamber 124 may be placed in the walls 126 of elution device 1422 as shown. When aqueous solution 122 comes into contact with polymer membrane 1410, the dissolvable polymer membrane is dissolved. The resulting solution, comprising the dissolvable polymer and any aerosol particles collected on or within the dissolvable polymer ("the eluate"), is preferably collected in an eluate reservoir 128 as shown. Optionally the aqueous solution 122 may be delivered as an effect of gravitational force to the polymer membrane 1410 by turning the connected sampling device 1402 and elution device 1422 upside down.

One of the advantages of the present invention is that the sampling device with the dissolvable polymer is preferably configured to have a low breathing resistance, a high aerosol particle and pathogen collection efficiency and is rapidly dissolvable in non-toxic aqueous solution to completely relase the pathogen for the subsequent detection assay upon elution. As a non-limiting example, polymer membrane 1410 may comprise an electrospun nanofiber mat, comprising fibers of the dissolvable polymer.

In some embodiments the dissolvable polymer membrane contain ligands or ligand-coated capture beads. A variety of ligands are available and are suitable for use. Non-limiting examples include antibodies, aptamers, peptides and mannose binding lectins.

In some embodiments the dissolvable polymer membrane may contain agents or detergents to increase stability during collection and improve solubility during elution. Non-limiting examples include Triton X-100, Tween, SDS, dichlorodiphenyltrichloroethane (DDT), chaotropic salts, Dithiothreitol (DTT), acids and/or bases, pH buffer salts, beads, or any combinations thereof.

Aqueous solution 122 in chamber 124 may contain lysing agents or detergents and may be configured to create a lysate. Non-limiting examples of lysing agents or detergents include Triton X-100, Tween, SDS, dichlorodiphenyltrichloroethane (DDT), chaotropic salts, Dithiothreitol (DTT), acids and/or bases, pH buffers, beads, solvents, or any combinations thereof. In a preferred embodiment the aqueous solution has a pH below 6.5 to rapidly dissolve the chitosan/PEO nanofiber mat. In another preferred embodiment the aqueous solution is a TRIS-EDTA buffer with a pH above 8.0 and directly compatible with nucleic acid amplification tests (NAATs) such as PCR.

FIGS. 2A-D are illustrative, exemplary, non-limiting diagrammatic side elevation views of the sampling device and the elution device from FIG. 1, illustrating the different steps of the procedure. Components with the same numbers as in FIG. 1 have the same or at least similar function.

Figure 2:
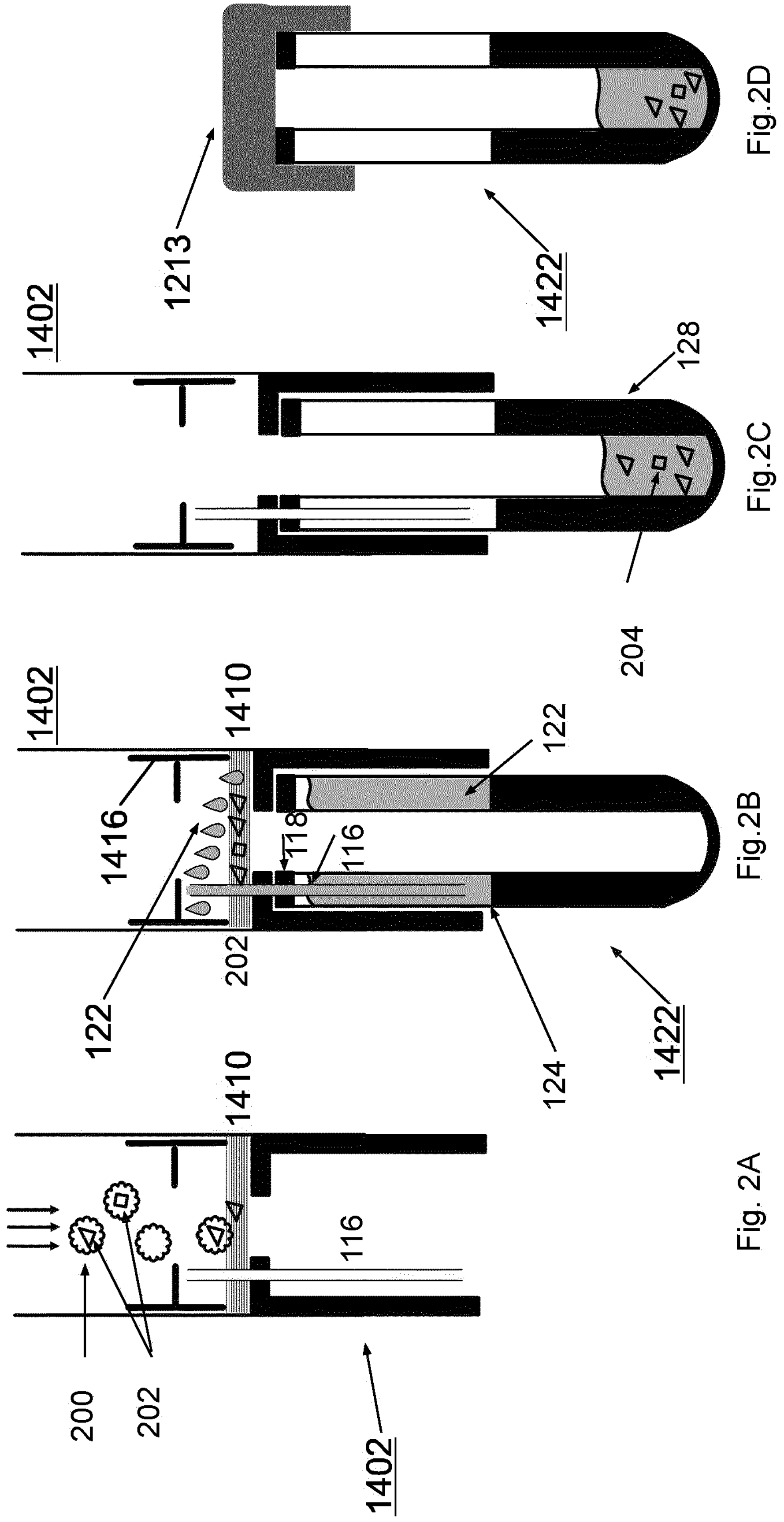
FIG. 2A-D are exemplary, diagrammatic side elevation views of the sampling device and the elution device from FIG. 1 illustrating the different steps of the procedure including (A) aerosol particles collection, (B) dissolution and elution of the captured pathogens, (C) retrieving of the eluate in the elution device, and (D) covering the elution device with a threaded lid.

FIG. 2A depicts a human breath aerosol particle 200 containing different pathogens 202 which are deposited on polymer membrane 1410 in the collection step. By pathogens 202 it is meant molecules and/or structures of a pathogen thereof, optionally including an entire pathogen and/or fragments thereof. By "aerosol", it is meant a breath sample comprising solid or liquid particles of any size suspended in gas as described herein. FIG. 2A shows sampling device 1402 without elution device 1422.

In the subsequent step, depicted in FIG. 2B, sampling device 1402 is connected to elution device 1422. Needle 116 pierces septum 118, enabling aqueous solution 122 in overpressure chamber 124 to flow into sampling device 1402 to dissolve polymer membrane 1410 that contains the collected pathogens 202. In an optional embodiment the aqueous solution 122 may be delivered as an effect of gravitational force to the polymer membrane 1410 by turning the connected sampling device 1402 and elution device 1422 upside down.

Next, depicted in FIG. 2C, the eluate 204 containing the pathogens is collected in the eluate reservoir 128. After the elution, elution device 1422 can be disconnected from the sampling device 1402. Elution device 1422 may be capped or covered with a threaded closure 1213 such as a lid for storage until further processing, as shown in FIG. 2D. For example, elution device 1422 may be transported with the sample to a central laboratory for subsequent analysis of the pathogen biomarkers.

Figure 3:
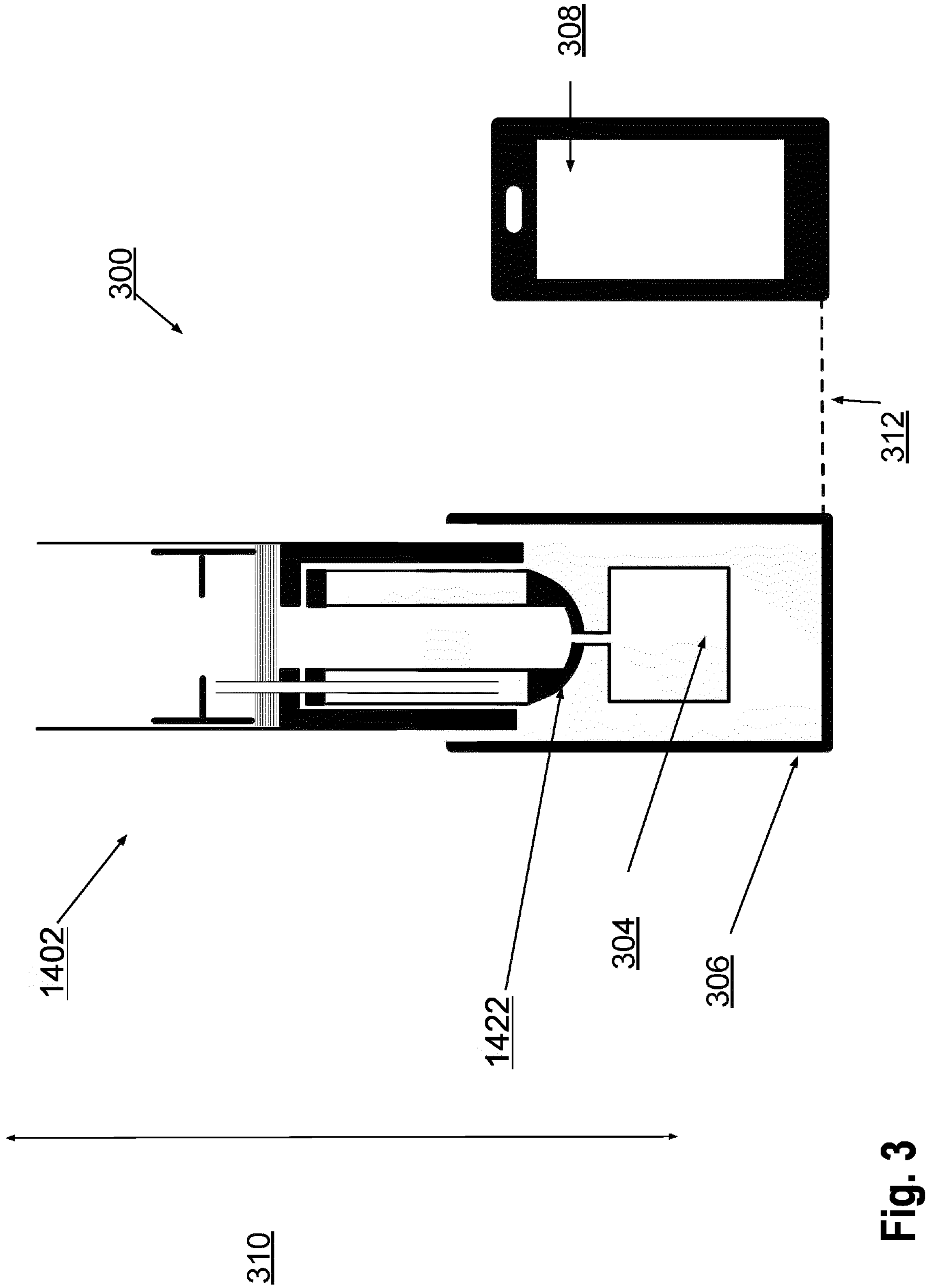
FIG. 3 is a diagrammatic view of the sampling device and elution device embodying the present invention using a microfluidic assay to detect the pathogens, a detector to read the signal from the microfluidic assay and a data entry, processing and presentation unit.

FIG. 3 depicts an illustrative, exemplary, non-limiting system, combining the sampling device 1402 and the elution device 1422 with a detection device 306 as shown herein. Components with the same numbers as in FIGS. 1 and 2A-2D have the same or at least similar function. As shown, a system 300 comprises sampling device 1402 and elution device 1422 as shown. System 300 preferably further comprises a detection device 306. Detection device 306 can hold an assay system 304 which provides a signal that is then read or detected by said detector 306. Detector device 306 is preferably in communicative connection with a computational device 308. Computational device 308 may comprise an external data entry, processing and presentation system for example, to allow results to be read locally and/or in real time by medical personnel. Optionally sampling device 1402, elution device 1422 and/or assay 304 comprise a test cartridge 310 as shown that can be entered into detection device 306 for the read-out. Computational device 308 may be in wireless, wired, visual and/or other suitable communication with detector 306 through a connection 312 as shown.

Assay 304 is preferably configured as a microfluidic assay in microfluidic communication with elution device 1422. A variety of microfluidic assays are available and are suitable for use. Non-limiting examples include immunoassays, isothermal amplification assay, PCR, nucleic acid hybridization, CRISPR-based assays, and sequencing. In a preferred embodiment the microfluidic assay is an isothermal amplification assay.

A variety of detectors 306 to read the assay signal are suitable for use. Non-limiting examples include fluorescence detectors, luminescence detectors, photometric detectors, or image sensors. In an optional but preferred embodiment the detector is a multi-color fluorescence detector.

A variety of external data entry, processing and presentation systems are available and suitable for use as or in combination with computational device 308. Non-limiting examples include smartphones, tablet computers, laptops, computers or other mobile processing units. The data entry, processing and presentation system can be connected in a variety of ways including but not limited to WiFi, Bluetooth, and USB and a variety of protocols can be used such as HL7, ASTM, FHIR standards.

Without wishing to be limited in any way, one of the advantages of the present invention is that the user enters clinical patient information in the data entry, processing and presentation computational device 308 which will be combined with pathogen data from detection device 306 in a clinical prediction rule. A non-limiting example is the combination of CRB-65 (confusion, respiratory rate, blood pressure, age) combined with the detected pathogen for clinical prediction of mortality risk in community-acquired pneumonia.

Figure 4:
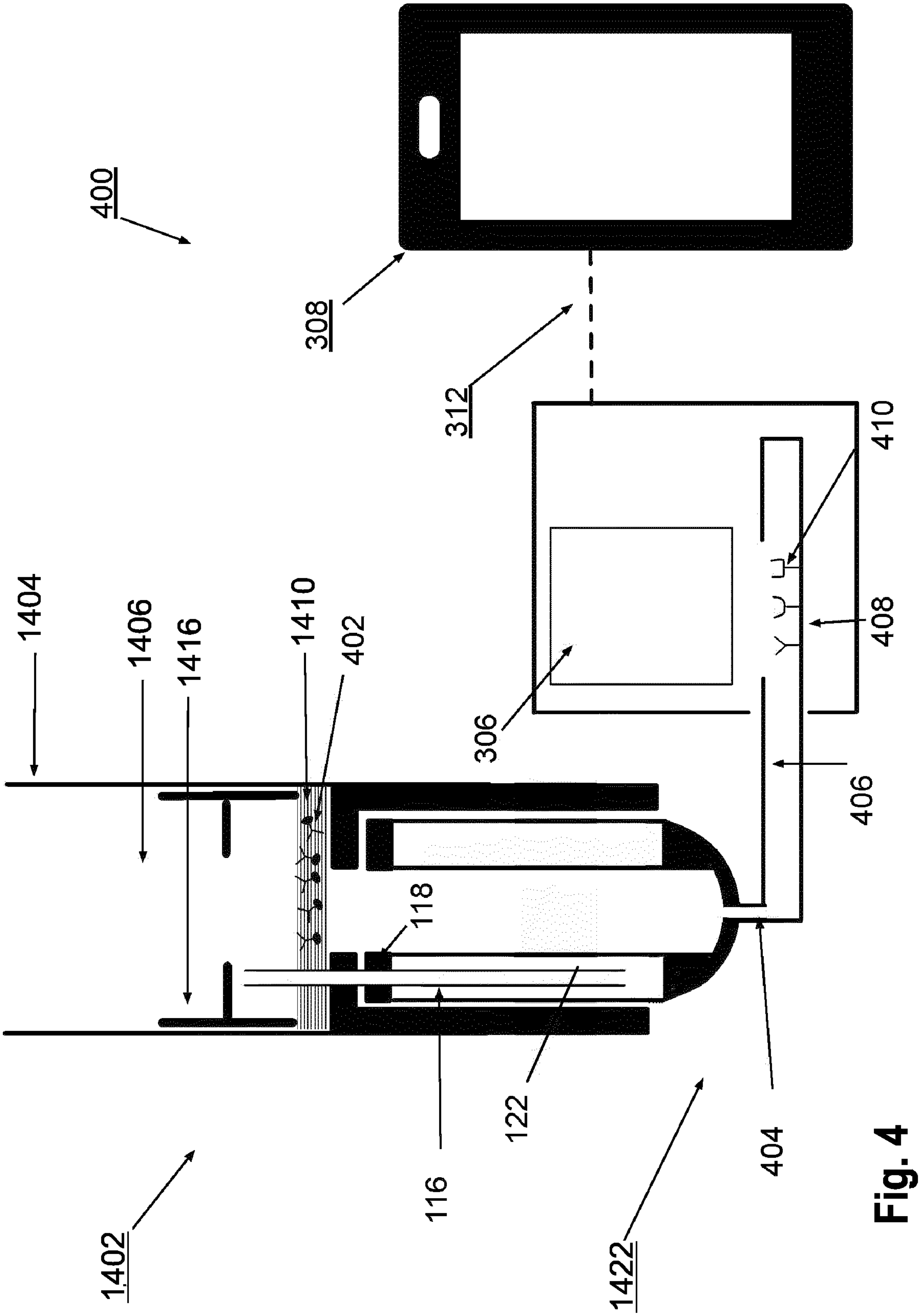
FIG. 4 is a diagrammatic side view embodying the present invention from FIG. 3 using a lateral flow immunoassay as a microfluidic assay to detect the pathogens, a camera-based detector to read the signal and a mobile tablet computer as a data entry, processing and presentation unit.

FIG. 4 is a non-limiting, exemplary, illustrative and specific example of an embodiment based on FIG. 3. Components with the same numbers as in FIGS. 1, 2A-2D and FIG. 3 have the same or at least similar function. A system 400 comprises polymer membrane 1410, which in this embodiment preferably further comprises capture reagents with detection labels 402. Polymer membrane 1410 is preferably contained in sampling device 1402 as shown. As shown, breath flows through airflow path 1406, such that breath particles and aerosols as shown impinge on polymer membrane 1410. Pathogens as described herein then may be captured by polymer membrane 1410 alone and/or in combination with capture reagents with detection labels 402.

When elution device 1422 is placed in fluid communication with sampling device 1402, preferably needle 116 pierces a septum 118. Aqueous solution 122 may then dissolve or otherwise disrupt polymer membrane 1410 as previously described. Aqueous solution 122 with dissolved polymer membrane 1410, pathogen markers if present and optionally capture reagents with detection labels 402 then flow through a fluid channel 404, preferably placed at the bottom of elution device 1422.

From fluid channel 404, the liquid preferably flows to an immunoassay-based microfluidic assay 406. Microfluidic assay 406 comprises a detection zone 408 and capture reagents 410 to detect the pathogens.

In some embodiments microfluidic assay 406 comprises a lateral flow assay. If capture reagents with detection labels 402 are present, the capture reagents are expected to bind to pathogen biomarkers. In some embodiments such labels are fluorescent nanoparticles coupled to antibody ligands that bind pathogen antigens. After the capturing and dissolution of the dissolvable polymer membrane 1410, the pathogen biomarker-capture reagent-detection labels complexes are expected to travel to the detection zone 408 in the microfluidic assay 406, where they are captured by secondary capture reagents 410 at a detection zone 408. In an exemplary embodiment the capture reagents are antibodies or other ligands that specifically bind to a pathogen antigen, the labels are fluorescent nanoparticles and the secondary ligand is an antibody that binds to the same pathogen antigen but to a different epitope. In some embodiments several different capture reagents with detection labels 402 may be present, and several different capture reagents 410 may be immobilized at a detection zone 408 to detect several different pathogens in a multiplex assay. Detection device 306 can hold and read the detection zone 408 which provides a signal. Detector device 306 is preferably in communicative connection with a computational device 308 through a connection 312 as shown.

FIG. 5 shows a non-limiting, exemplary, illustrative method of analyzing human breath aerosols. As shown in a method 500, the flow preferably begins with exhalation of a human subject into the sampling device 502. Such breath, along with breath particles comprising pathogen biomarkers, are preferably then allowed to impinge on and/or otherwise contact a polymer membrane 504. The polymer membrane comprises an aqueous liquid dissolvable polymer material. At this point, the method may continue after transfer of the polymer membrane to an elution device. Alternatively, the method continues as described below.

Next, the polymer membrane is preferably dissolved with aqueous solution from the elution device 506. At this point, the method may continue after transfer of the elution device to a detection system.

The liquid is then allowed to contact a microfluidic assay within a detection system, which is preferably then able to detect such pathogen biomarkers 508. The data is preferably transmitted to a data entry, processing and presentation unit 510. The clinical prediction based on the received pathogen data and clinical data entered by the user in an algorithm may then be calculated 512. The final result may then be presented to the user 514.

Figure 6:
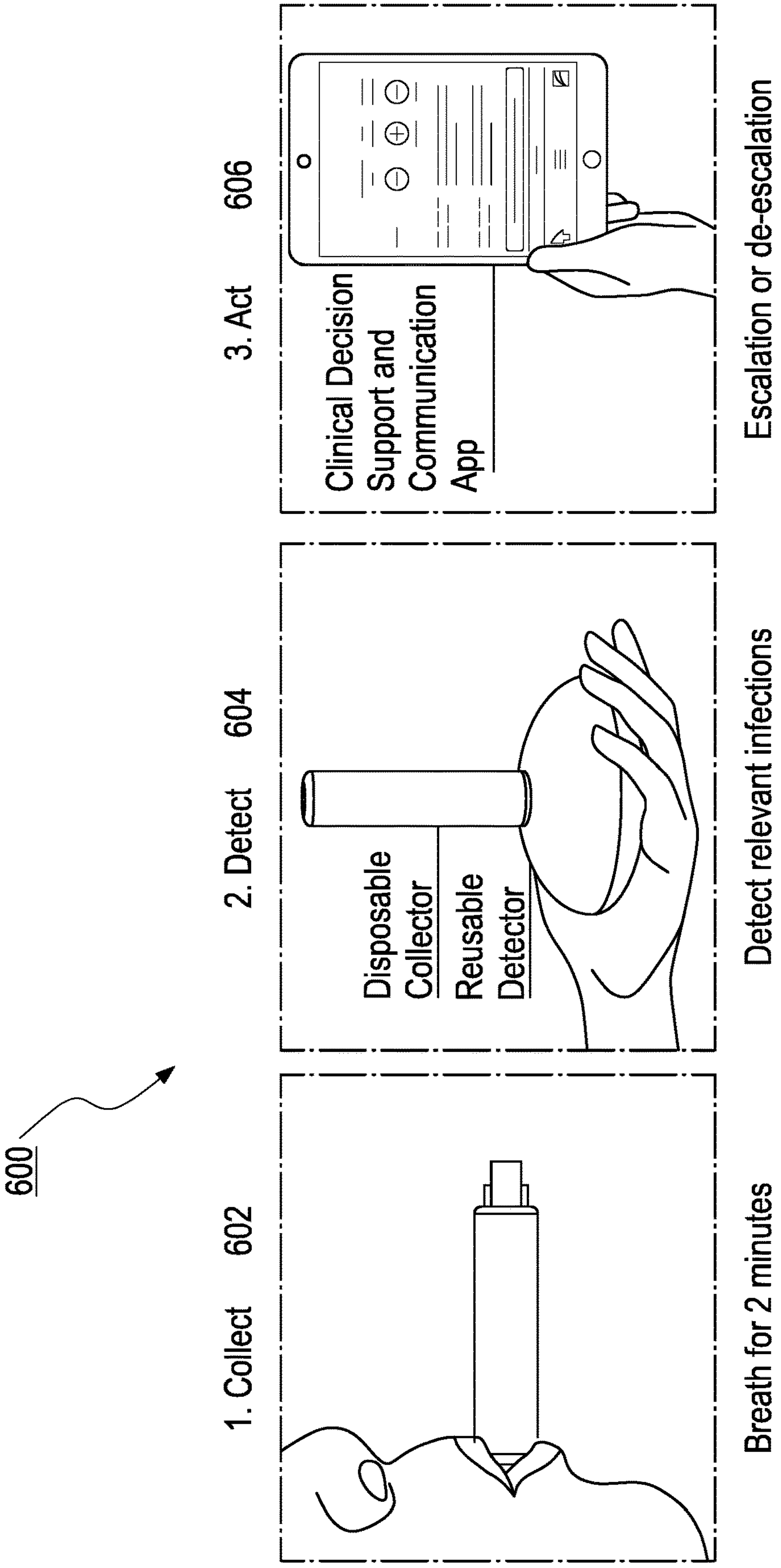
FIG. 6 shows a non-limiting exemplary simplified flow, with the sampling device and detector, and computational device being shown in a photograph.

FIG. 6 shows a non-limiting exemplary simplified flow, with the sampling device, detector, and computational device being shown in a photograph. In a flow 600, collection of the breath begins when the subject (or patient) exhales into the sampling device at 602. At 604, the sampling device is preferably brought into fluid communication with a detector, which is able to detect one or more breath pathogens. At 606, the results from the detector may be sent to a remote device as shown.

Figure 7A:
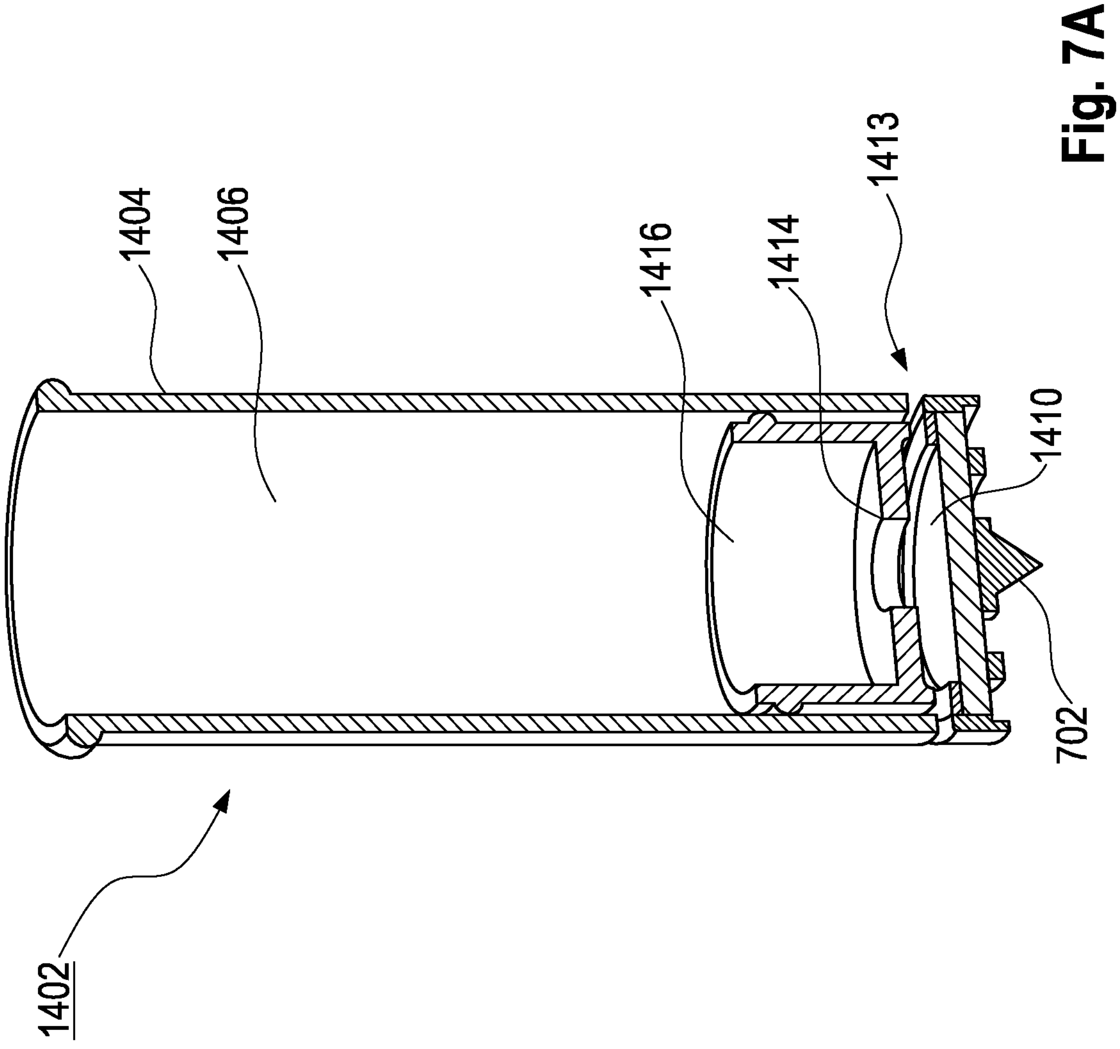
FIGS. 7A and 7B show alternative, optional embodiments of the previously described sampling device and elution device, respectively.
Figure 7B:
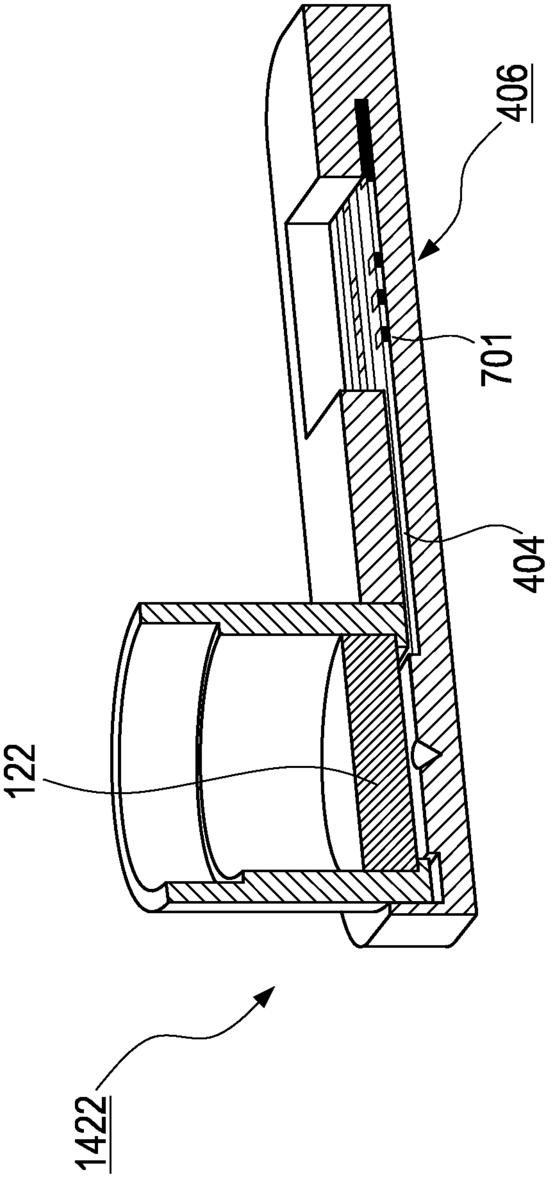

FIGS. 7A and 7B show alternative, optional embodiments of the previously described sampling device and elution device, respectively. Components with the same numbers as in FIGS. 1, 2A-2D, 3 and 4 have the same or at least similar function. FIG. 7A shows sampling device 1402 in an optional embodiment, shown in a cut-away perspective. In this optional embodiment, sampling device 1402 preferably comprises, an accelerator 1414, a plurality of air slits 1413 and a piercer 702. Air slits 1413 support reduced pressure for breathing into sampling device 1402. Piercer 702 may support collection and concentration of liquid with the dissolved material from polymer membrane 1410, by enabling an aqueous solution reservoir to be pierced.

FIG. 7B shows elution device 1422 in an optional embodiment, shown in a cut-away perspective. In this optional embodiment, aqueous solution 122 preferably is brought into contact with the previously described polymer membrane 1410, after which the liquid with the dissolved polymer membrane components flows to a fluid channel 404. Such a liquid contains pathogen biomarkers, breath particles, pathogens and portions thereof, and so forth.

Via the fluid channel 404, the liquid then flows to a microfluidic assay 406 comprising a lateral flow assay. In some embodiments the microfluidic assay 406 comprises one or more immunochromatographic test strips 701 as shown, for detecting one or more pathogen biomarkers.

Figure 8:
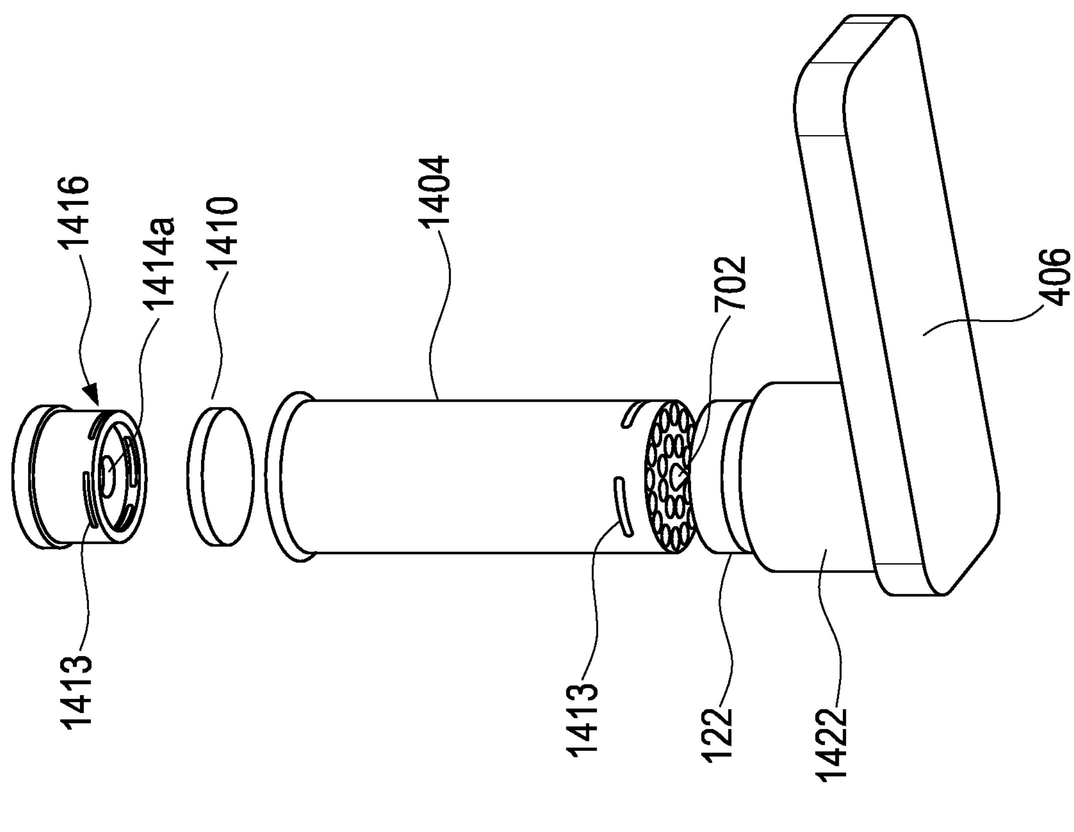
FIG. 8 shows an exploded view of an optional embodiment of the previously described sampling device and elution device, and biomarker assay.

FIG. 8 shows an exploded view of an optional embodiment of the previously described sampling device and elution device, biomarker assay. Components with the same numbers as in FIGS. 1, 2A-2D, 3, 4 and 7A-7B have the same or at least similar function.

In this embodiment, a tubular housing 1404 comprises the previously described polymer membrane 1410 which is fixed with a retainer element 1416. Said retainer element contains a plurality of air slits 1413 and one or several nozzles **1414*a* to accelerate the aerosol particles. The tubular housing 1404 also contains a plurality of air slits 1413 aligned with the air slits from said retainer element 1416. The elution device 1422 preferably comprises the aqueous solution 122 in a reservoir and is connected to the microfluidic assay 406. The tabular housing comprises piercer 702 as shown. Piercer 702 preferably causes the reservoir of elution device 1422 to be ruptured, such that an aqueous solution comes into contact with polymer membrane 1410 and dissolves the dissolvable polymer therein. The eluate may then flow to said microfluidic assay 406** for detecting one or more pathogen biomarkers.

Figure 9:
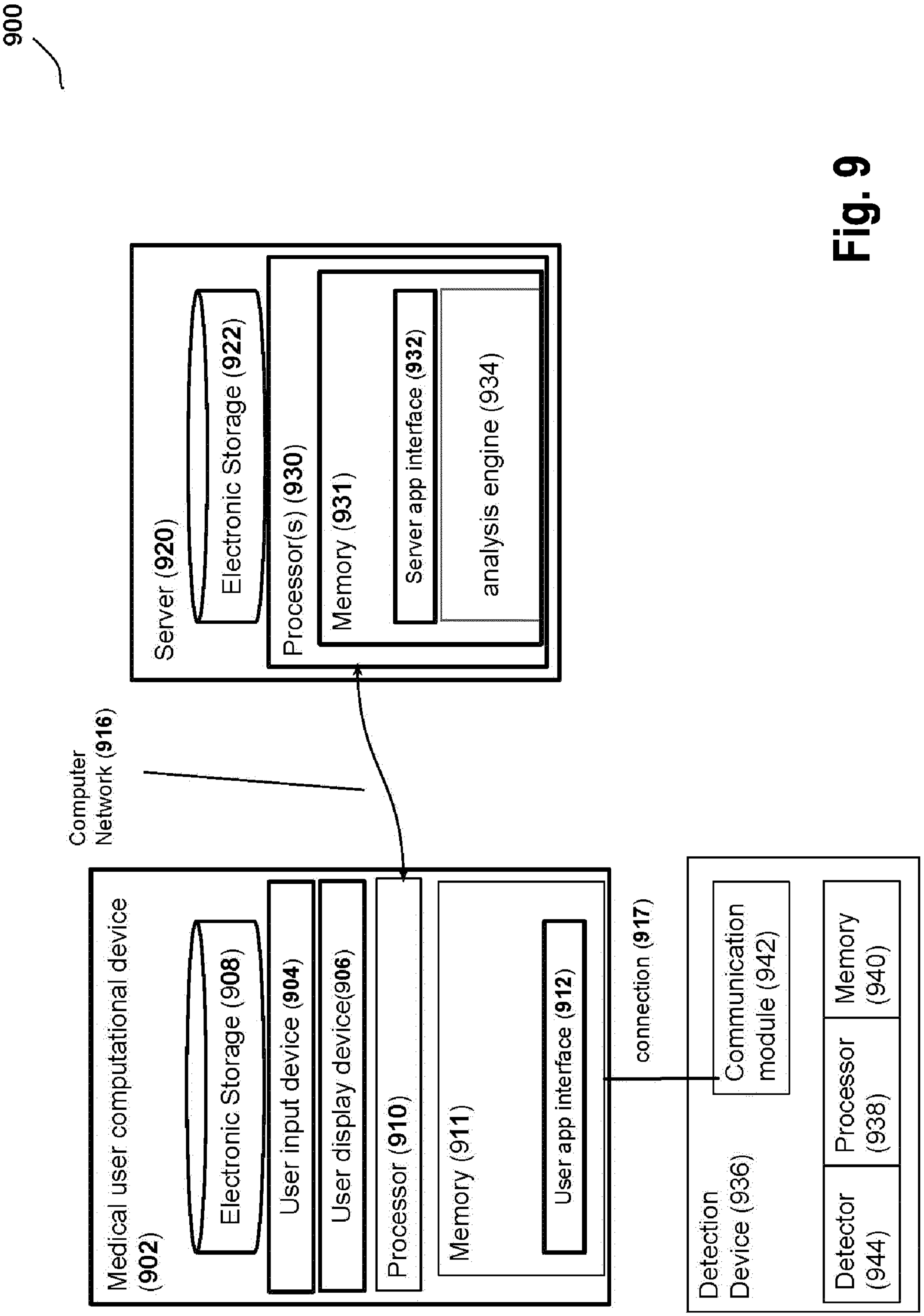
FIG. 9 shows an exemplary non-limiting computational system for detecting one or more pathogen biomarkers from a breath sample to preferably provide an actionable diagnosis.

FIG. 9 shows an exemplary non-limiting computational system for detecting one or more pathogen biomarkers from a breath sample to preferably provide an actionable diagnosis. As shown in a system 900, a medical user computational device 902 is in at least data communication with a detection device 936, through a wired or wireless connection 917. Detection device 936 may also comprise the assay and detector as described herein, and/or may comprise additionally or alternatively other components as described herein. Detection device 936 is preferably at least able to read the results of the assay detecting the presence of one or more pathogen biomarkers. Medical user computational device 902 preferably receives the results of the assay from detection device 936.

Medical user computational device 902 may also communicate with a server 920, for example to transmit the results from detection device 936, and/or to obtain patient information from server 920. Such information may be sent alone or in combination with an analysis of the results, for example according to a clinical calculation of the risk factor(s) and/or overall risk that a particular condition may present to a particular patient. In a non-limiting example the user enters clinical patient information in the medical user computational device 902 which will be combined with patient information from server 920 and pathogen data from detection device 936. Alternatively or additionally, detection device 936 may communicate directly with server 920. A non-limiting example is the combination of CURB-65 criteria (confusion, blood urea nitrogen, respiratory rate, blood pressure, age) entered in the medical user computational device 902 combined with pathogen data including results for Flu A/B, RSV, Coronavirus, Rhinovirus, Adenovirus, *Streptococcus pneumoniae, Haemophilus influenzae, Mycobacterium tuberculosis, Mycoplasma pneumonia, Chlamydia pneumonia, Bordetella pertussis*, Human metapneumovirus, Parainfluenza, *Pneumocystis jirovecii*, Group A *Streptococcus* (GAS), *Legionella pneumophila* from the detection device 936 combined with laboratory results for CRP, PCT and chest X-ray results from a server 920 to predict the mortality risk in pneumonia and propose appropriate treatment.

Medical user computational device 902 may include a user input device 904, a user app interface 912, and a user display device 906. The user input device 904 may optionally be any type of suitable input device including but not limited to a keyboard, touchscreen, microphone, mouse, or other pointing device and the like. Preferably user input device 904 includes a microphone and a keyboard, mouse, or keyboard mouse combination.

User app interface 912 may be used to interact with detection device 936, for example to transmit a command to obtain assay results from detection device 936 and/or assay conditions or parameters for example. User app interface 912 may also be used to show patient information and/or analysis from server 920.

Detection device 936 optionally and preferably comprises a communication module 942 for transmitting at least assay results to medical user computational device 902.

Medical user computational device 902 also comprises a processor 910 and a memory 911. Functions of processor 910 preferably relate to those performed by any suitable computational processor, which generally refers to a device or combination of devices having circuitry used for implementing the communication and/or logic functions of a particular system. For example, a processor may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processor may further include functionality to operate one or more software programs based on computer-executable program code thereof, which may be stored in a memory, such as a memory 911 in this non-limiting example. As the phrase is used herein, the processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

Also optionally, memory 911 is configured for storing a defined native instruction set of codes. Processor 910 is configured to perform a defined set of basic operations in response to receiving a corresponding basic instruction selected from the defined native instruction set of codes stored in memory 911. For example and without limitation, memory 911 may store a first set of machine codes selected from the native instruction set for receiving a request for information from the user through user app interface 912, a second set of machine codes selected from the native instruction set for transmitting such information from server 920, a third set of machine codes selected from the native instruction set for requesting results from detection device 936 and a fourth set of machine codes selected from the native instruction set for receiving such results from detection device 936.

Similarly, server 920 preferably comprises processor 930 and memory 931 with machine readable instructions with related or at least similar functions, including without limitation functions of server 920 as described herein. For example and without limitation, memory 931 may store a first set of machine codes selected from the native instruction set for receiving a request for patient information and/or analysis from medical user computational device 902, a second set of machine codes selected from the native instruction set for executing functions of analysis engine 934, and a third set of machine codes selected from the native instruction set for transmitting such information and/or analysis to medical user computational device 902. Optionally memory 931 stores a fourth set of machine codes selected from the native instruction set for receiving assay result information from medical user computational device 902.

Optionally and preferably, detection device 936 comprises a processor 938 and a memory 940, which may be combined in the form of a SOC (system on chip) for example, or as any suitable microprocessor combination. Instructions stored on memory 940 are executed by processor 938. For example and without limitation, memory 940 may store a first set of machine codes selected from the native instruction set for determining one or more assay results, a second set of machine codes selected from the native instruction set for receiving a request for such results from medical user computational device 902, and a third set of machine codes selected from the native instruction set for transmitting such results to medical user computational device 902.

Also optionally and preferably, detection device 936 comprises a detector 944 for detecting the results of an assay, such as for example an indicator of the presence of a pathogen biomarker in the breath sample.

Figure 10:
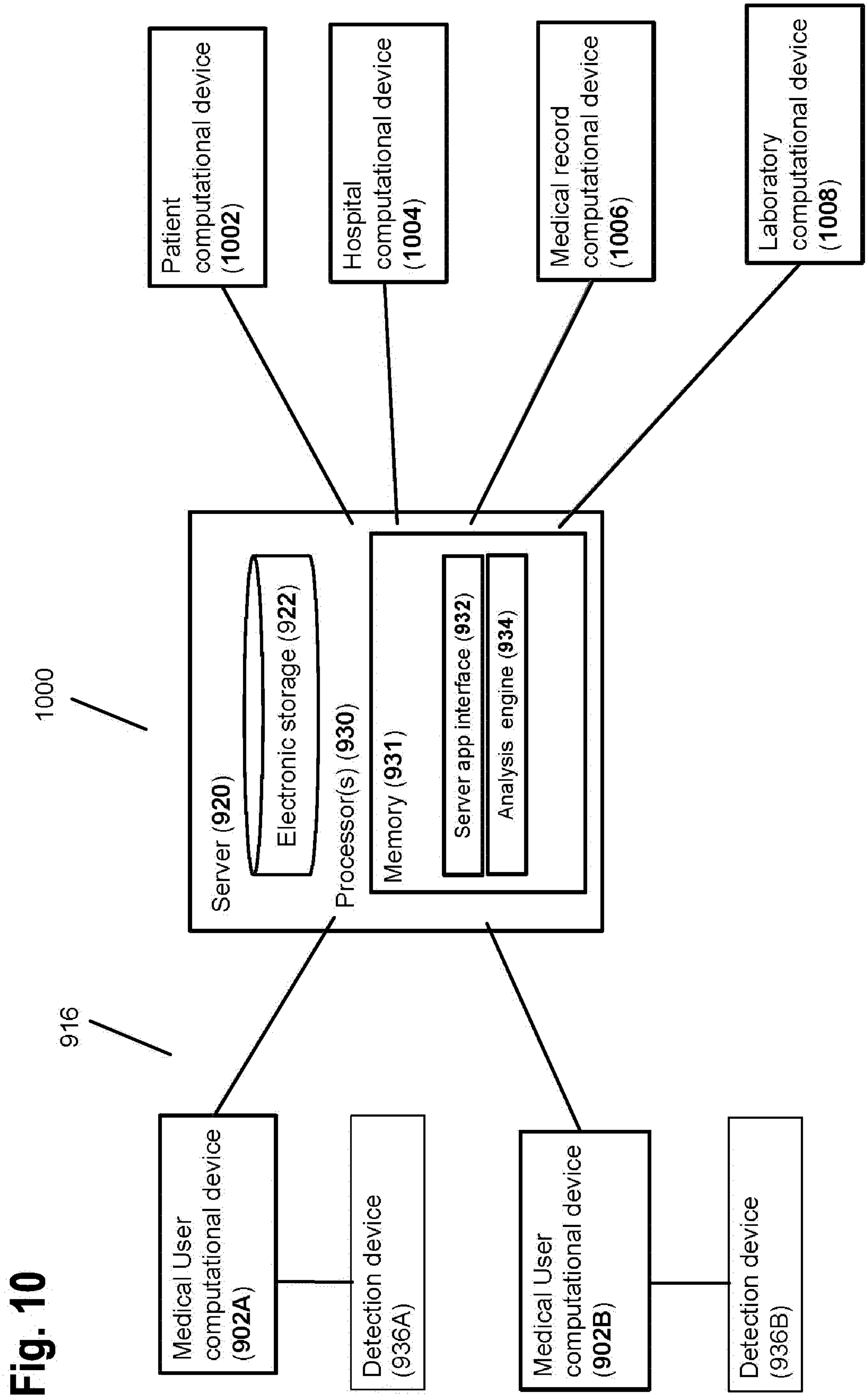
FIG. 10 shows a non-limiting exemplary system for receiving multiple such assay results, analyzing them (optionally in combination with other information), and then transmitting and/or storing them.

FIG. 10 shows a non-limiting exemplary system for receiving multiple such assay results, analyzing them (optionally in combination with other information), and then transmitting and/or storing them. Components with the same reference numbers as FIG. 9 have the same or at least similar function.

A system 1000 features a plurality of medical user computational devices 902, of which two are shown, medical user computational device 902A and medical user computational device 902B, for the sake of illustration only and without any intention of being limiting. System 1000 also features a plurality of detection devices 936, of which two are shown, detection device 936A and detection device 936B, for the sake of illustration only and without any intention of being limiting. Each of detection devices 936A and 936B is preferably able to at least read assay results and transmit them to medical user computational devices 902A and 902B, respectively. Each such detection device 936 may also be able to receive an aerosol sample and detect the result of at least one assay as described herein, for detecting the presence of at least one respiratory pathogen. As previously described, each of medical user computational devices 902A and 902B is preferably able to transmit such results to server 920, and is also optionally able to receive a clinical analysis and/or patient information in return. As previously described, each of detection devices 936A and 936B are optionally further able to directly transmit such results to server 920 (not shown).

Server 920 is preferably also able to transmit such results to a patient computational device 1002. Optionally patient computational device 1002 is able to transmit patient details, including without limitation one or more patient symptoms, current medical history, previous medical history and the like. Server 920 is optionally and preferably also able to communicate with a hospital computational device 1004, for example to transmit the results and/or clinical analysis, and/or to receive patient information. Hospital computational device 1004 may be any suitable medical facility computational device. Server 920 is optionally and preferably also able to communicate with a medical record computational device 1006, for example to obtain patient medical record information and/or to transmit the assay results, optionally with an analysis as described herein. Server 920 is optionally and preferably also able to communicate with a laboratory computational device 1008, for example to transmit the results and/or clinical analysis, and/or to receive laboratory results. Laboratory computational device 1008 may be any suitable laboratory facility computational device.

Figure 11A:
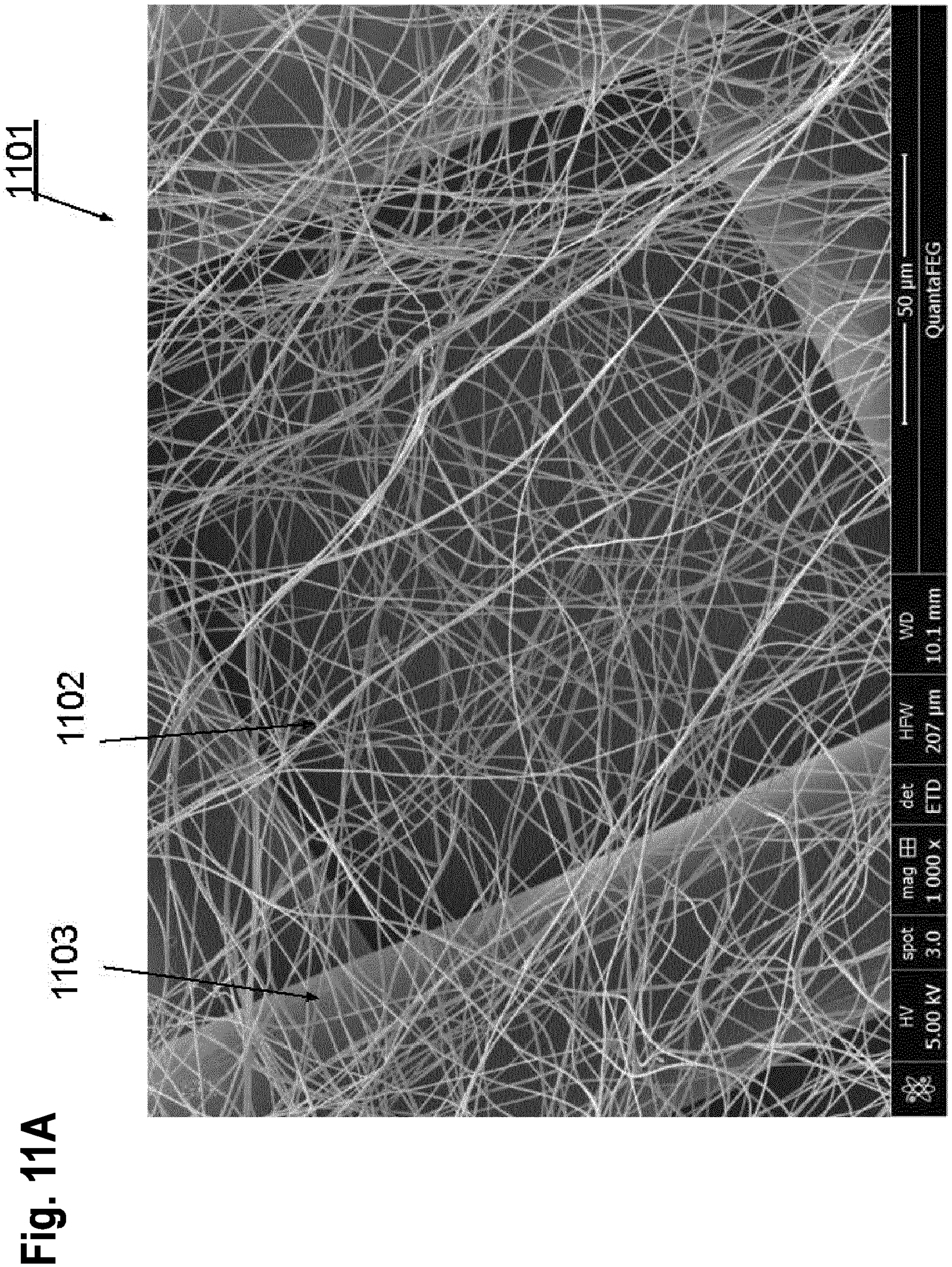
FIGS. 11A and 11B show non-limiting exemplary scanning electron microscope (SEM) images of a polymer membrane consisting of a chitosan/polyethylene oxide (PEO) nanofiber mat on a polyethylene terephthalate (PET) support mesh prior to exposure to breath aerosols (A) and post exposure to breath aerosols (B).
Figure 11B:
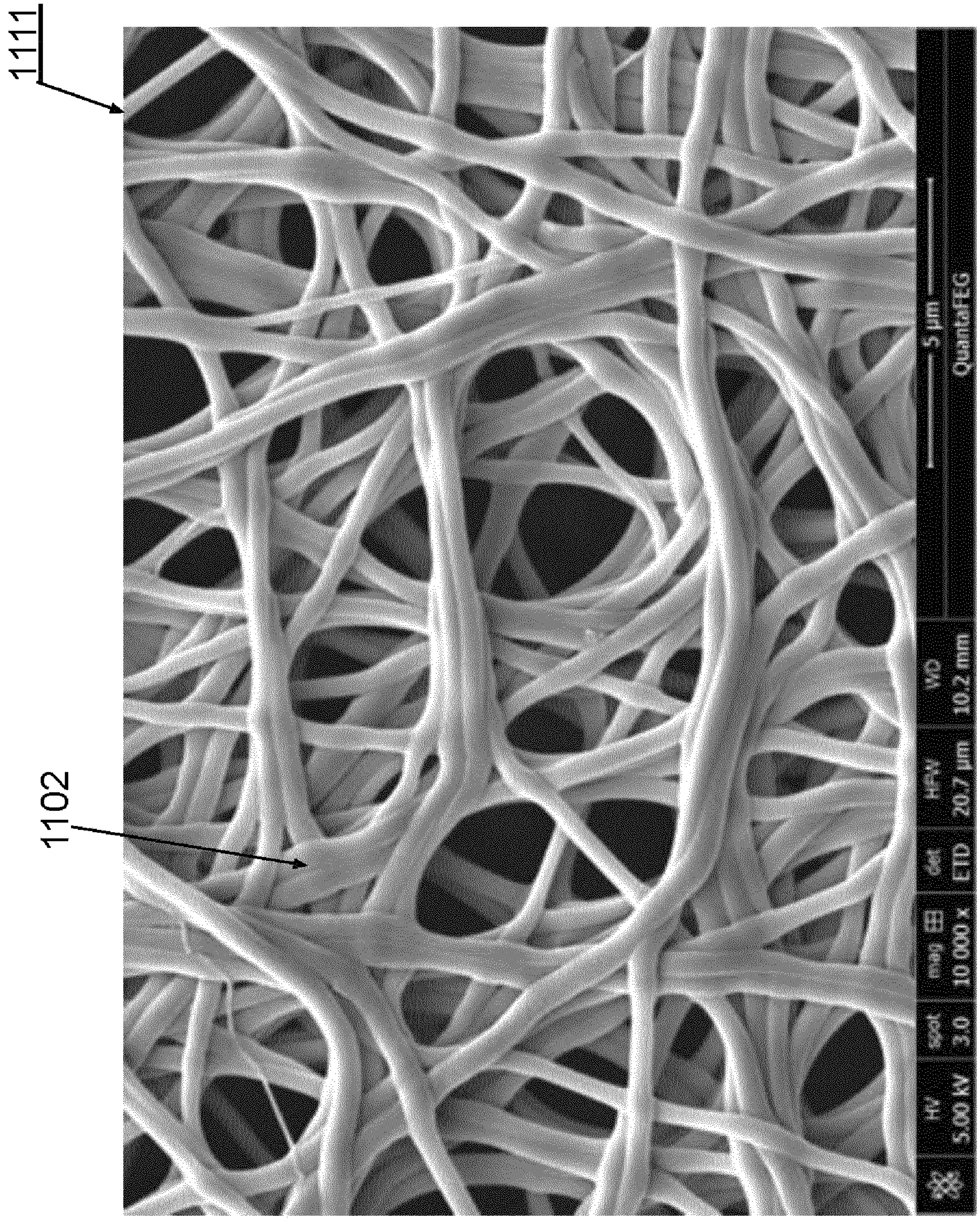

FIGS. 11A and 11B show non-limiting exemplary scanning electron microscope (SEM) images of electrospun fibers on a support, before (FIG. 11A) and after (FIG. 11B) exposure to human breath aerosols. Image 1101 shows an electrospun chitosan/polyethylene oxide (PEO) (mass ratio 8:2) nanofiber mat with fibers 1102 of roughly 300 nm diameter, on a polyethylene terephthalate (PET) support mesh 1103 (such as Sefar Nitex 03-130/52, Sefar AG, Switzerland), prior to exposure to breath aerosols. SEM Image 1111 shows the same chitosan/polyethylene oxide (PEO) fiber mat 1102 post exposure to a human breath aerosols for 2 minutes. Except for some swelling of the material, the nanofiber mat shows high stability to human breath aerosols and remains its pathogen collection efficiency.

Preferably, the aqueous solution dissolvable polymer membrane used in all of the various sampling devices described herein includes PVA fibers electrospun on a PVA foil. Preferably, the PVA has a viscosity range of 4 to 65 mPa*s (viscosity is measured at 4% in $H_2O$ at 20° C.), and a degree of hydrolysis of 70 to 93%. In an exemplary embodiment the PVA has a viscosity of 8 mPa*s and a degree of hydrolysis of 88%.

Figure 12A:
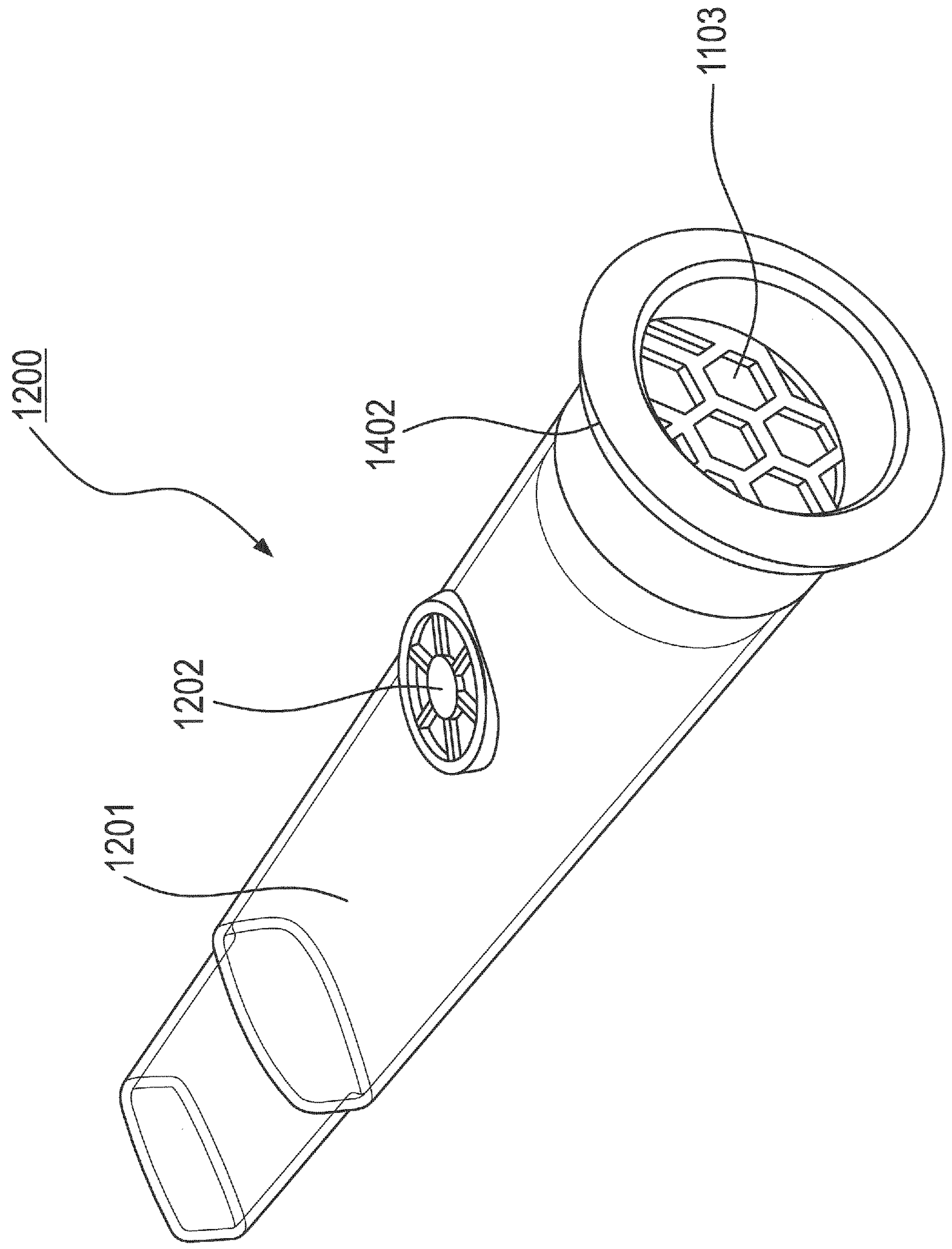
FIGS. 12A and 12B show an alternative, optional embodiment of the previously described sampling device (A) for use for collection, mailing to a lab, elution with the elution device, testing in the lab and result transmission to the patient (B).
Figure 12B:
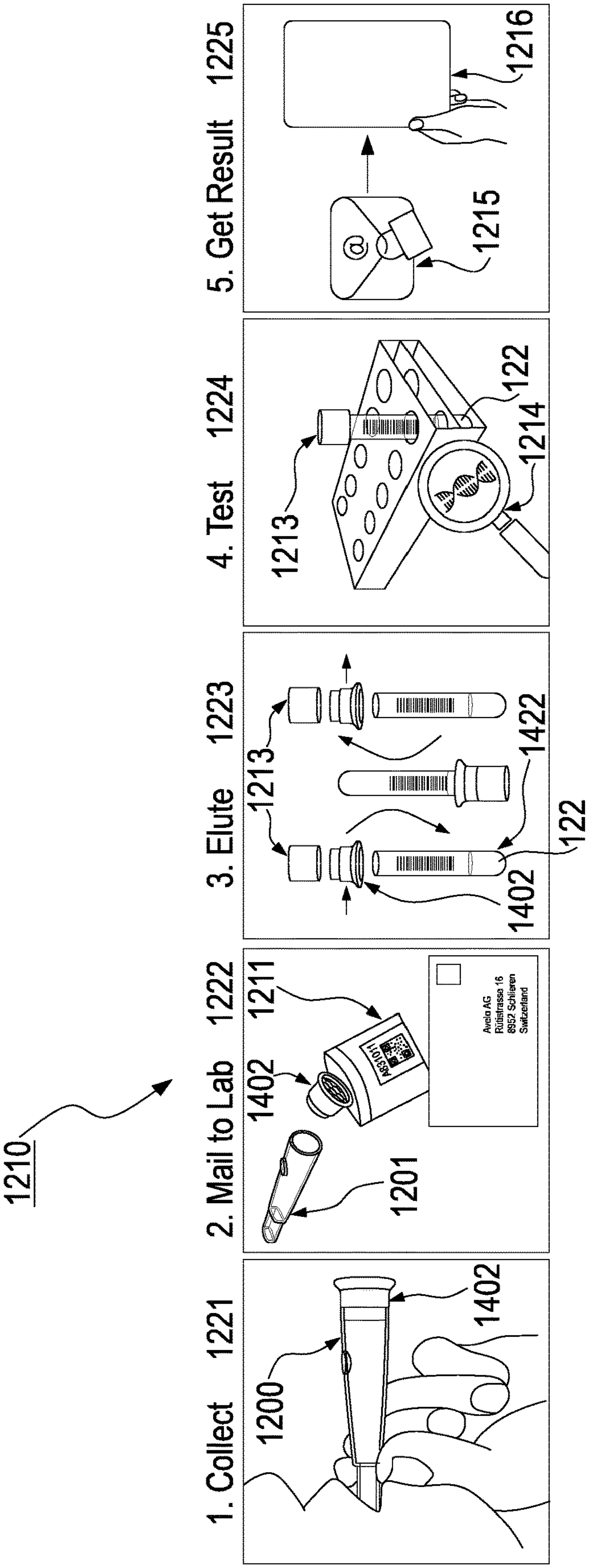

FIGS. 12A and 12B show an alternative, optional, exemplary embodiment of the previously described sampling device. As shown with regard to FIG. 12A, a device 1200 contains a mouthpiece 1201, an optional inhalation valve 1202 and a sampling device 1402 that contains the dissolvable polymer membrane on a support mesh 1103. In a preferred embodiment the polymer membrane is a nanofiber mat on a support mesh to collect aerosol particles, for example as shown in FIG. 11A. FIG. 12B shows an exemplary, non-limiting, centralized laboratory testing use case process 1210 where device 1200 is used for the collection 1221 of breath aerosol. The process continues with subsequent mailing 1222 of the sampling device 1402 that contains said polymer membrane with the collected aerosol particles in a labelled sample bag 1211 to a centralized laboratory facility. In the elution process 1223, the sampling device 1402 is inserted between a threaded lid 1213 and elution device 1422 which is a standard tube containing aqueous solution 122. By way of example the tube containing the aqueous solution 122 and the lid 1213 can be custom made or be a standard centralized laboratory tube containing PCR transport media such as tubes from the cobas PCR Media kit (Roche Diagnostics, Switzerland) or the universal viral transport (UVT) system (Becton Dickinson, USA).

After connecting the sampling device 1402 to the tube 1422 on the one end, and the sampling device 1402 and the threaded lid 1213 on the other end, the system is turned upside down to dissolve the aqueous solution dissolvable polymer membrane by bringing said dissolvable polymer membrane into contact with the aqueous solution as an effect of gravitational force. After the dissolution and elution of the collected pathogens and/or biomarkers, the sampling device 1402 can be removed and disposed, and the resulting liquid eluate in the elution device 1422 that contains the pathogens and/or biomarkers can be tested 1224 in the standard centralized laboratory workflow preferably using automated high-throughput analyzers. Non-limiting examples include molecular assays that analyze the pathogen nucleic acid 1214 in the eluate and antigen detection assays. Upon completion of the testing, the result is sent back to the patient or healthcare provider 1225 via secure communication channels 1215. By way of example results can be submitted via the internet with protocols based on widely available interoperability standards for result transmission such as HL7, ASTM, or FHIR. By way of example results are presented to the patient or healthcare provider with an application running on a portable device like a tablet computer or a smartphone 1216. By way of example the sampling device 1402 can also be transported and/or stored together with the threaded lid 1213 and the elution device 1422 with the aqueous solution 122 as the aqueous solution may help to stabilize the pathogen and/or biomarkers during storage and/or transportation. The aqueous solution can also inactivate the pathogen for safe transportation and storage.

Figure 13:
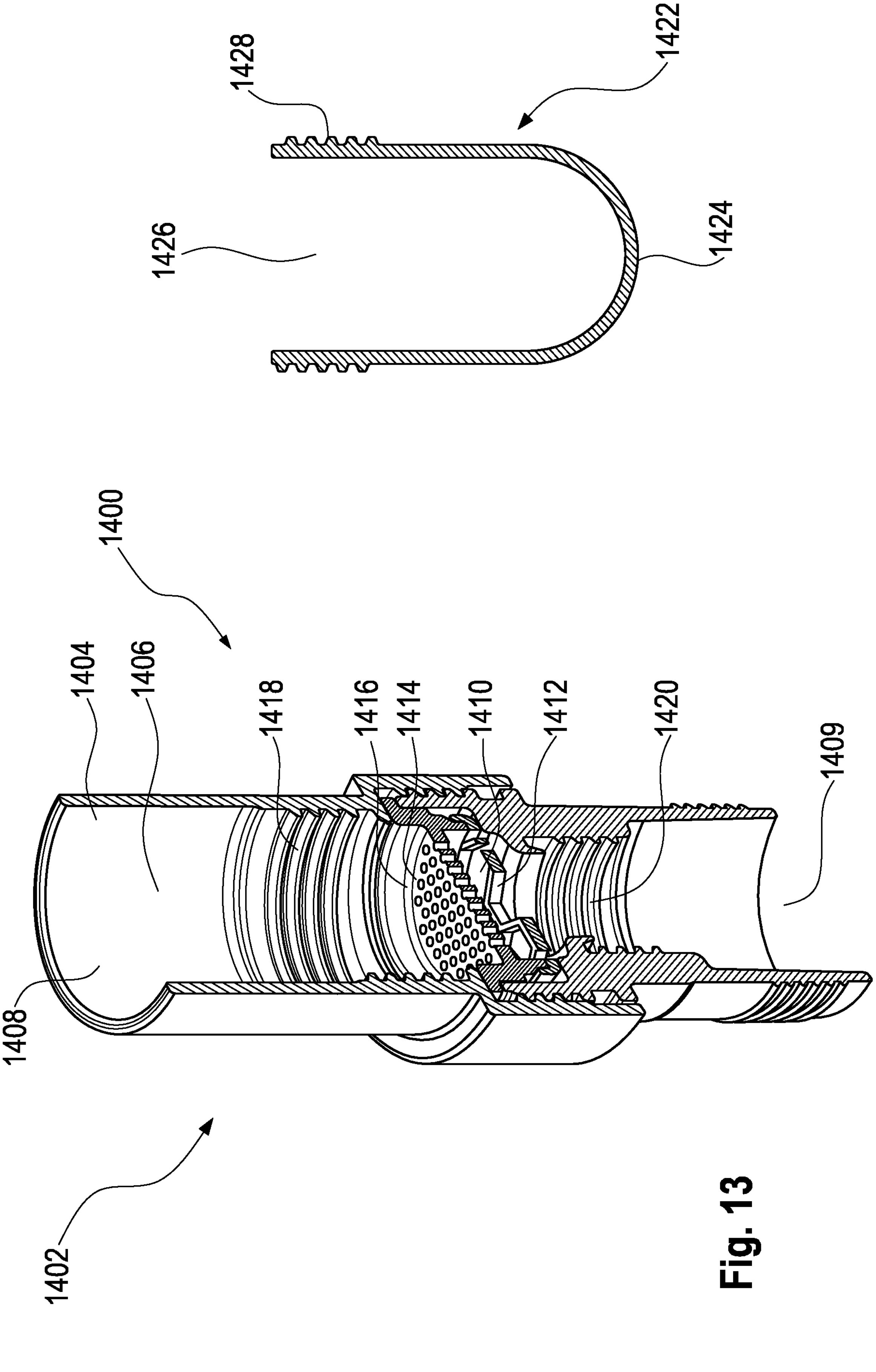
FIG. 13 shows a perspective cut-away side elevation view of an alternative, optional embodiment of the previously described sampling device.

FIG. 13 shows an alternative, optional embodiment of the previously described sampling device. The sampling device 1402 of FIG. 13 comprises a tubular housing 1404 having a flow inlet 1408 at one end and a flow outlet 1409 at the other end opposite the flow inlet 1408. Aerosols exhaled from a subject flow along an airflow path 1406 from the flow inlet 1408 to the flow outlet 1409. The tubular housing 1404 is preferably of a two-piece design. The two parts are held together by means of a threaded or clamped engagement of the two parts. To this end, an external thread provided at the upper end of the lower part engages an internal thread provided at the lower end of the upper part.

An aqueous solution dissolvable polymer membrane 1410 that is supported by a membrane holder 1412 which extends into tubular housing 1404, in a plane perpendicular to the airflow path 1406 in FIG. 13. Upstream of the polymer membrane 1410 is provided an accelerator 1414. The accelerator 1414 preferably includes one or a plurality of nozzles which act as an accelerator 1414 as the nozzles accelerate the aerosol particles as it flows through the nozzles 1414*a*. The nozzles 1414*a* of the accelerator 1414 are preferably equidistantly spaced apart from each other across the inner diameter of the tubular housing 1404. Only by way of comparison, the upstream topography of the accelerator 1414 resembles that of a honeycomb structure due to its converging nozzle inlets.

The accelerator 1414 is held in position by a retainer element 1416, which, according to the exemplary embodiment shown in FIG. 13, is clamped between the upper part and the lower part of the tubular housing 1404. The retainer element 1416, which is preferably formed as a one-piece part with the accelerator 1414, snaps into the membrane holder 1412 to clamp the polymer membrane 1410 and to keep it in place.

The accelerator 1414 preferably includes 83 nozzles 1414*a*. The number of nozzles 1414*a* may depend on the diameter of the tubular housing 1404, but preferably is in a range of 25 to 200. The nozzles 1414*a* each have a nozzle opening which has preferably a diameter of 0.78 mm and have a convergent, tapered nozzle inlet geometry (Venturi-type geometry) to promote acceleration of the aerosol particles flow through the nozzles 1414*a* and to reduce the breathing resistance during aerosol particles sampling. The diameter of the nozzles 1414*a* may depend on the total number nozzles 1414*a*, but may preferably range from 0.2 mm to 1.5 mm. Preferably the sum of the area of all nozzle openings in the accelerator 1414 is in the range from 20 to 65 $mm^2$.

Upstream of the accelerator 1414 is provided a thread 1418 which may be used for the purpose of engaging a closure (not shown) with the thread to close off the flow inlet 1408. The thread 1418 may be an internal or external thread depending on the type of closure. For example, the thread 1418 may be an internal thread provided on the inner surface of the housing 1404 to introduce a threaded plug or lid to close off the flow inlet 1408.

Another thread 1420 is provided downstream of the polymer membrane 1410 which may be used to screw into the tubular housing 1404 an elution device 1422 used to dissolve the polymer membrane 1410.

As is also shown in FIG. 13, the elution device 1422 is a tube with a closed end 1424 and an open end 1426 opposite the closed end 1424. An external thread 1428 is provided in proximity of the open end 1426, which may be brought into engagement with the internal thread 1420 provided downstream of the polymer membrane 1410 inside of the tubular housing 1404 of the sampling device 1402.

It is conceivable to close off the flow outlet 1409 by engaging a closure with the thread 1420, and to use thread 1418 for engagement with an elution device 1422.

Instead of a thread 1420, the sampling device 1402 may well be provided with any type of engagement means to releasably engage the elution device 1422 with the tubular housing 1404 of the sampling device 1402. Such engagement means may be clamping means, piercing means, such as the needle 116 shown in FIG. 1, threaded engagement means, such as shown in FIG. 13, or other types of connecting or fastening means that are suitable to releasably engage the elution device 1422 with the tubular housing 1404 of the sampling device 1402 in order to provide a fluidic communication pathway between the elution device 1422 and the interior of the tubular housing 1404 of the sampling device 1402.

The same or similar considerations may be applied to the thread 1418.

The sampling device 1402 shown in FIG. 13 is optimized towards efficient collection of pathogens present in human breath aerosol particles with low breathing resistance and subsequent dissolution of the polymer membrane 1410 followed by easy collection of the sample in a elution device 1422 such as a standard lab tube.

Figure 14A:
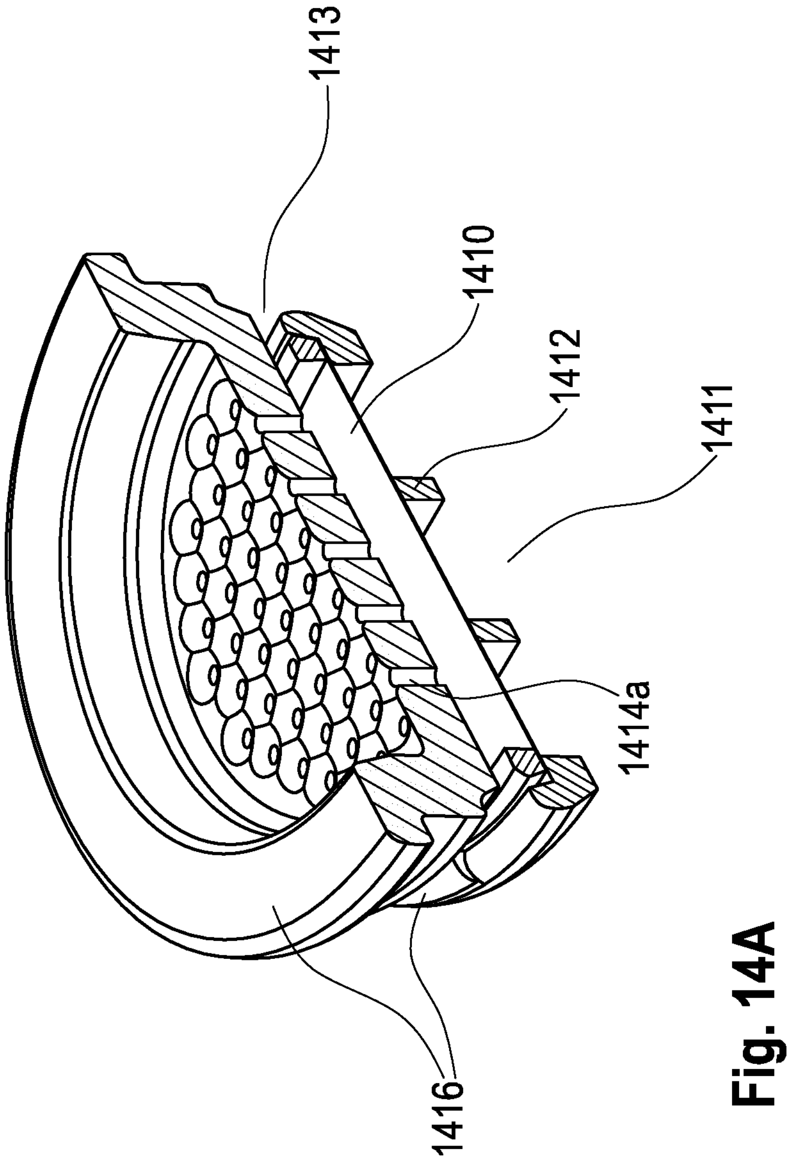
FIG. 14A shows a perspective cut-away side elevation view of a detail of the sampling device shown in FIG. 13.

FIG. 14A shows a detail of the sampling device 1402 of FIG. 13 in a perspective, cut-away side elevation. The accelerator 1414 in the embodiment of FIG. 14A includes a plurality of nozzles 1414*a* and is provided upstream of the polymer membrane 1410. The polymer membrane 1410 is supported by the membrane holder 1412 below the accelerator 1414. The membrane holder 1412 is configured such that a large enough surface of the polymer membrane 1410 is exposed to allow for dissolution of the polymer membrane 1410 when brought into contact with an aqueous solution provided by the elution device 1422. For that purpose, once the elution device 1422 is screwed into the tubular housing 1404 of the sampling device 1402, the sampling device 1402 together with the elution device 1422 is turned upside down, thus causing the aqueous solution to flow out of the elution device 1422, into the tubular housing 1404 of the sampling device 1402 and into contact with the polymer membrane 1410 by effect of gravitation via the openings 1411 in the membrane holder 1412.

The accelerator 1414 is spaced apart from the polymer membrane 1410 in a flow direction of the aerosol to allow aerosol to flow first through the nozzles 1414*a* followed by escape of air radially outwardly through the slit 1413. Due to the heavier weight of the aerosol particles contained in the aerosol, these particles impinge onto the polymer membrane 1410, whereas the main airflow of the air without these particles escapes radially outwardly through the slit 1413. The slit 1413 may therefore be considered as a bypass and is preferably arranged around at least a part of the circumference of the polymer membrane 1410.

Figure 14B:
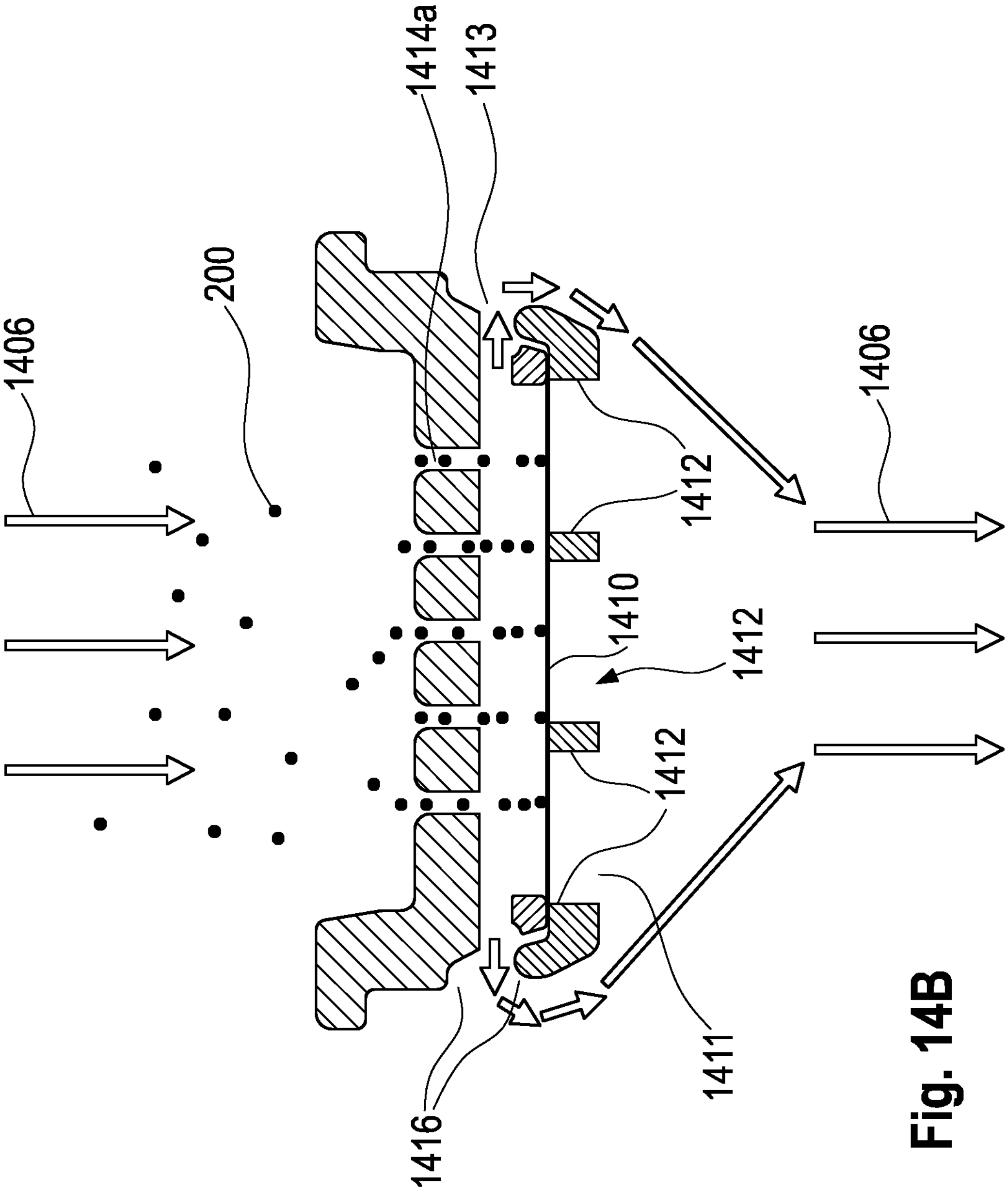
FIG. 14B shows the aerosol particles and air flow path through the sampling device part shown in FIG. 14A.

FIG. 14B shows the airflow path 1406 of the aerosol and the aerosol particles 200 contained in the aerosol. The aerosol containing the aerosol particles 200 first flow through the accelerator 1414. The aerosol particles 200 then impinge onto the polymer membrane 1410, whereas the airflow continues to flow radially outwardly through the slit 1413 until the airflow is deflected on the inner surface of the tubular housing 1404 and converges again below the polymer membrane 1410 to again flow along the main airflow path 1406.

Example 1—Evaluation of the Sampling Device for the Collection of *Mycobacterium* from Simulated Breath Aerosols with Elution and Detection Using a Commercial Tuberculosis PCR Assay This non-limiting Example relates to an illustrative sampling device and elution device for the collection of *Myco-*

*bacterium* from simulated human breath aerosols with elution and subsequent detection using a commercial TB assay.

Materials and Methods

Dissolvable Polymer Membrane

The nanofibers were prepared by mixing dissolved chitosan and PEO at a mass ratio of chitosan to PEO of 8:2 followed by free surface electrospinning of the solution with a Nanospider NS Lab 500 (Elmarco, Czech Republic) onto a PET support mesh (SEFAR MEDIFAB 07-20/23). The resulting electrospun chitosan/PEO nanofiber mat had a thickness of approximately 10 μm and nanofibers had a diameter of approximately 300 nm as illustrated in FIG. 11A. The nanofiber mat on the support mesh was cut by punching circular membranes with a diameter of 19 mm.

Sampling Device

The 3D printed custom made sampling device housing out of polyamide 12 (PA2200, EOS GmbH, Germany) had an outer diameter of 22 mm, an inner diameter of 20 mm and a length of 85 mm. The polymer membrane containing the polymer material on the PET support mesh was fixed between a custom made PA2200 retainer elements a membrane holder and positioned in the flow path of the sampling device housing. The sampling device design is illustrated in FIG. 12A.

Simulated Human Breath Aerosols

*Mycobacterium bovis* BCG (1.91×10ex8 cfu/ml) was diluted at different concentration in 0.067 M phosphate buffer pH 6.8 and nebulized using a Cirrus2 nebuliser (Intersurgical, UK) into a custom-build, glass chamber (length 60 cm, diameter 8 cm) using HEPA-filtered air at 6 l/min. Molecular grade water was nebulized in the same way as a negative control. Air flow rate was measured using a SFM3300-AW digital flow meter (Sensirion, Switzerland).

Sampling

The outlet of the glass chamber was connected to the inlet of the sampling device for 2 minutes sampling. The weight difference of the Cirrus2 nebuliser and the *Mycobacterium bovis* BCG cfu/ml value was used to calculate the bacterial load exposed to sampling device. The outlet of the sampling device was connected to a 5 ml BioSampler (SKC, USA) containing buffer.

Elution

After the aerosol sampling, the sampling device (consisting of the two PA2200 retainer elements and the nanofiber mat on the PET support mesh) was connected to the elution device 1422 as illustrated in FIG. 12B. The elution device is a standard laboratory tube with a diameter of 16 mm and the sampling device 1402 is designed so that it releasably engages with the elution device 1422. The tube contains 1.5 ml of 0.067 M Phosphate Buffer with a pH of 6.8 as a elution liquid. After connecting the elution device 1422 with the sampling device 1402 and a lid 1213, the arrangement is turned upside-down for 2 minutes to eluate the collected BCG bacteria. After turning the arrangement again the eluate is collected in the elution device by removing the sampling device and by closing the elution device with the lid.

DNA Detection

DNA was isolated from 0.5 ml of the aqueous solution from the elution device using FluoroLyse (Hain Lifescience, Germany) and BCG was detected using IS6110-directed PCR using FluoroType MTB (Hain Lifescience, Germany) on a FluoroCycler 12 real-time PCR cycler (Hain Lifescience, Germany) as described in the user instructions.

Results

Figure 15:
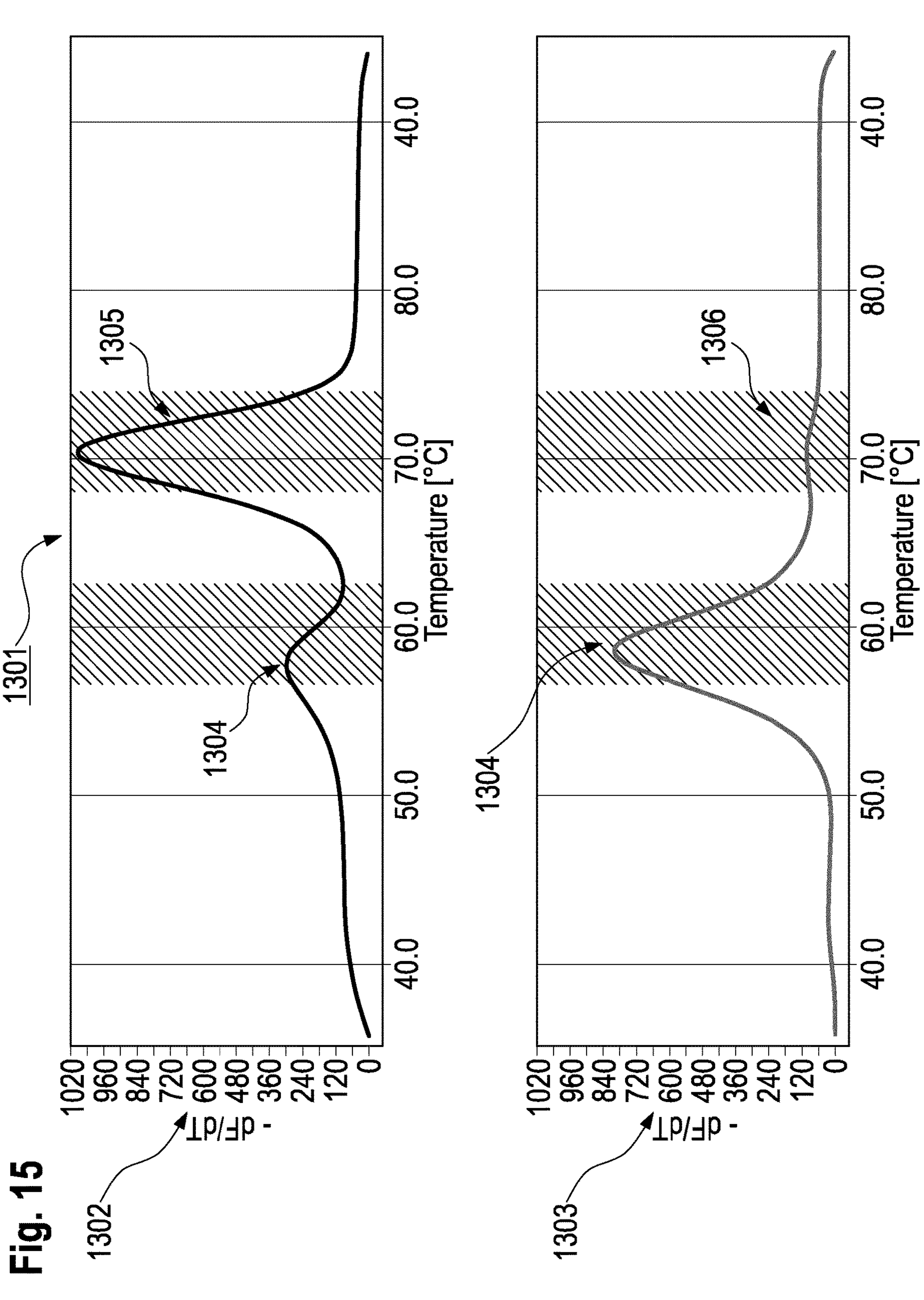
FIG. 15 shows results of a PCR assay when used in combination with the sampling device of the present invention.

FIG. 15 shows typical melt curve charts 1301 for a clearly positive 1302 and a negative sample 1303. The positive sample melt curve chart 1302 shows a peak for the internal assay control DNA 1304 as well as a peak for the BCG IS6110 amplicon 1305. The negative sample melt curve chart 1303 shows only the peak for the internal assay control DNA 1304 but no peak for the BCG IS6110 amplicon 1306. The limit of detection (LOD) of the experiment was 402 cfu in 12 liter of aerosol or 33 cfu BCG per liter aerosol. Since BCG has only one copy of the IS6110 gene, this equals an LOD of 2 cfu *M. tuberculosis* per liter aerosol when assuming sixteen IS6110 copies for *M. tuberculosis.*

Example 2—Measuring of Breathing Resistance

This non-limiting Example relates to an illustrative sampling device for the collection of human breath aerosol particles used for the determination of breathing resistance.

Materials and Methods

Dissolvable polymer membrane—The nanofibers were prepared in the same way as described in Example 1.

Sampling device—The sampling device was prepared in the same way as described in Example 1

Measurement of Breathing Resistance

Breathing resistance of the sampling device containing the dissolvable polymer membrane was measured by applying a constant airstream of 20 l/min and by measuring pressure drop by connecting an SDP800 differential pressure sensor (Sensirion, Switzerland) at the inlet and outlet of the sampling device using T-piece connectors.

Results

Breathing resistance of the sampling device with the dissolvable polymer membrane as a filter was 419 Pa. This breathing resistance is sufficiently low to collect exhaled breath without exposing the patient to stress.

Example 3—Sampling Device with Aerodynamics and Electrospun Nanofiber Mat

This non-limiting Example relates to an illustrative sampling device having aerodynamic nozzles with a dissolvable fiber polymer membrane.

Sampling Device Design and Production

The sampling device design is as shown in FIGS. 13, 14A and 14B. The size of the particles which can be collected with 50% efficiency (d50) is 0.9 μm. Thus, the sampling device reaches a high collection efficiency for aerosol particles at airflows larger than 30 l/min and for particles larger than 1 μm but at low breathing resistance.

Polymer Membrane Production

The polymer membrane with the nanofibers was prepared by needle electrospinning of a 10 wt % polyvinyl alcohol (PVA) aqueous solution. The synthetic, bio-compatible, nontoxic PVA has a viscosity range of 8 mPa*s and a degree of hydrolysis of 88%. The suspension was heated to >80° C. to dissolve the PVA and cooled down to ambient temperature after dissolution. Electrospinning was done on a Fluidnatek LE-100 (Nanoscience Instruments, Phoenix, AZ) onto a dissolvable polymer foil on a rotating drum collector. The resulting mean fiber diameter is 88-442 nm and the nanofiber mat has a thickness of 10-20 μm. The resulting polymer membrane consisting of nanofiber mat on the polymer foil is punched with a 21 mm diameter punching tool and placed inside the sampling device. The polymer membrane is placed in the membrane holder and clamped by the retainer element with the nanofiber mat facing the nozzle outlet.

Example 4—Characterisation of a Sampling Device from Example 3 for the Collection, Elution and Detection of *Mycobacterium* from Simulated Breath Aerosols in Combination with Three Molecular TB Assays This non-limiting Example relates to the optimized illustrative sampling device from Example 3 for the collection of *Mycobacterium* aerosol particles with elution using the elution device and subsequent detection using three commercial molecular TB assays.

Materials and Methods

Simulated Mycobacterial Aerosols

*Mycobacterium bovis* BCG stocks ($7.19\times10^6$ cfu/ml) were diluted 600-fold ("medium"), 1500-fold ("low"), and 7500-fold ("very low") in 7H9 broth supplemented with 10% Middlebrook OADC growth supplement. The same supplemented 7H9 broth but without BCG was used to generate "negative" samples. 150 to 170 mg of these BCG suspensions with different cell concentrations or the negative sample were nebulized with a Cirrus2 nebulizer (Intersurgical, UK) using HEPA-filtered air at 6 l/min to achieve average BCG levels of 1992 cfu ("medium"), 797 cfu ("low"), 159 cfu ("very low"), 0 cfu ("negative") in the aerosol. The nebulizer outlet was connected to a T-piece to dilute the aerosol with 6 l/min HEPA-filtered air to achieve a total mass flow of 12 l/min. Air flow rates were controlled with two SFC5500 mass flow controllers (Sensirion, Switzerland). The output of the T-piece with the diluted aerosol was connected to the inlet of the sampling device for 35 seconds of sampling per experiment.

Elution

After the collection of the aerosol particles, an elution device which is a standard laboratory tube containing 2 ml of 1× TE buffer pH 8.5 (10 mM Tris, 1 mM EDTA) was connected to the sampling device via the thread on the outlet side. The sampling device was closed with a plug via the thread on the inlet side. After closing of the sampling device with the laboratory tube and plug, the arrangement was turned upside-down for 2-4 minutes so that the TE buffer comes into contact with the polymer membrane to dissolve the polymer membrane to elute the collected BCG bacteria. After turning the arrangement again, the eluate runs into the elution device/tube and the sampling device was removed. The eluate in the tube was used for subsequent analysis with three molecular nucleic acid amplification tests (NAATs).

DNA Detection with Three Different NAATs

The liquid samples from the elution device were tested with 3 NAATs for IS6110-directed detection of BCG.

For the first test, GeneXpert MTB/RIF Ultra (Cepheid, USA), 1.5 ml Xpert Ultra Sample Reagent was directly added to 1 ml of eluate, vortexed for 10 seconds and incubated for a total of 15 minutes at ambient temperature. Between 5 and 10 minutes into the incubation period the sample was vortexed again for 10 seconds. After the incubation the entire volume of 2.5 ml was added to the test cartridge which was run on a GeneXpert GX-IV PCR analyzer.

Prior to the second and third tests, a simple heat lysis was performed by incubating 0.2 ml of eluate for 15 minutes at 95° C. at 1000 rpm in a heat block. After centrifugation for 5 minutes at 10000 rpm the supernatant was directly used as a sample for the two tests. 6 μL was used as a sample for the Hain FluoroType MTB (Hain Lifescience, Germany) run on a FluoroCycler 12 PCR cycler (Hain Lifescience, Germany) and tested as described in the user instructions. 30 μL was used as a sample for the isothermal Loopamp MTBC Detection Kit (Human Diagnostics, Germany) run on a LA-500 Loopamp Realtime Turbidimeter (Eiken, Japan) and tested as described in the user instructions.

Results

Table 1 shows the results of the 84 aerosol experiments for the sampling device and elution device in combination with the detection using the three NAATs. The negative aerosol collected with the sampling device and eluted with the elution device remained negative for all three tests in all experiments (N=21). Loopamp MTBC and FluoroType MTB delivered positive results for 100% of BCG containing aerosols at all three levels (medium, low and very low). This includes the "very low" level which demonstrates reproducible collection, elution and detection of a bacterial load of 159 cfu BCG in 6.4 litres aerosol. Xpert MTB/RIF Ultra detected all "medium" and "low" samples and 50% of the "very low" samples.

*M. tuberculosis* (Mtb) contains sixteen IS6110 gene copies whereas BCG contains only one IS6110 gene copy. Therefore the analytical sensitivity of Mtb is expected to be 16-times below the analytical sensitivity of BCG for these tests which suggests that the sampling device and the elution device together with NAATs is able to detect 10 cfu Mtb in 6.4 litres aerosol.

TABLE 1

| BCG Bacteria Aerosol | Average Input cfu | Average Air Vol | Sampling device & elution device with Loopamp ™ MTBC % | | Sampling device & elution device with Xpert ® MTB/RIF Ultra % | | Sampling device & elution device with FluoroType ® MTB % | | Sampling device & elution device with all tests % | |
|---|---|---|---|---|---|---|---|---|---|---|
| Level | BCG | L | Positive | Pos/N | Positive | Pos/N | Positive | Pos/N | Positive | Pos/N |
| Medium | 1992 | 6.3 | 100% | 9/9 | 100% | 6/6 | 100% | 6/6 | 100% | 21/21 |
| Low | 797 | 6.2 | 100% | 9/9 | 100% | 6/6 | 100% | 6/6 | 100% | 21/21 |
| Very low | 159 | 6.4 | 100% | 9/9 | 50% | 3/6 | 100% | 6/6 | 86% | 18/21 |
| Negative | 0 | 6.5 | 0% | 0/9 | 0% | 0/6 | 0% | 0/6 | 0% | 0/21 |

Example 5—Exhalation Flow Rate and Breathing Resistance of the Sampling Device from Example 3

Materials and Methods

Exhalation Air Flow Rate

Exhalation air flow rate was measured in 3 participants (2 female, 1 male) by connecting the sampling device to a SFM3300 mass flow sensor (Sensirion) and asking participants to inhale deeply and blowing/exhaling into the sampling device.

Pressure Drop Measurement

Breathing resistance of 10 sampling devices were measured by determining the pressure drop at different air mass flow rates between 10 and 80 l/min (80 measurements in total). Pressure drop over the sampling device was measured using a PREMASGARD 1115-I LCD (S+S Regeltechnik, Germany) differential pressure sensor. Air flow rates were controlled with a SFC5500 mass flow controller (Sensirion, Switzerland).

Results

Exhalation Flow Rate

Figure 16:
FIG. 16 shows exhalation flow rates of three different persons.

FIG. 16 shows exhalation flow rates of the 3 participants. Typical exhalation flow rates peaks were ranged between 40 and 70 l/min. Exhaled volume ranged from 1.2 to 4.1 l and the total volume ranged from 16 to 29 l for one minute of sampling.

Pressure Drop Measurement

Figure 17:
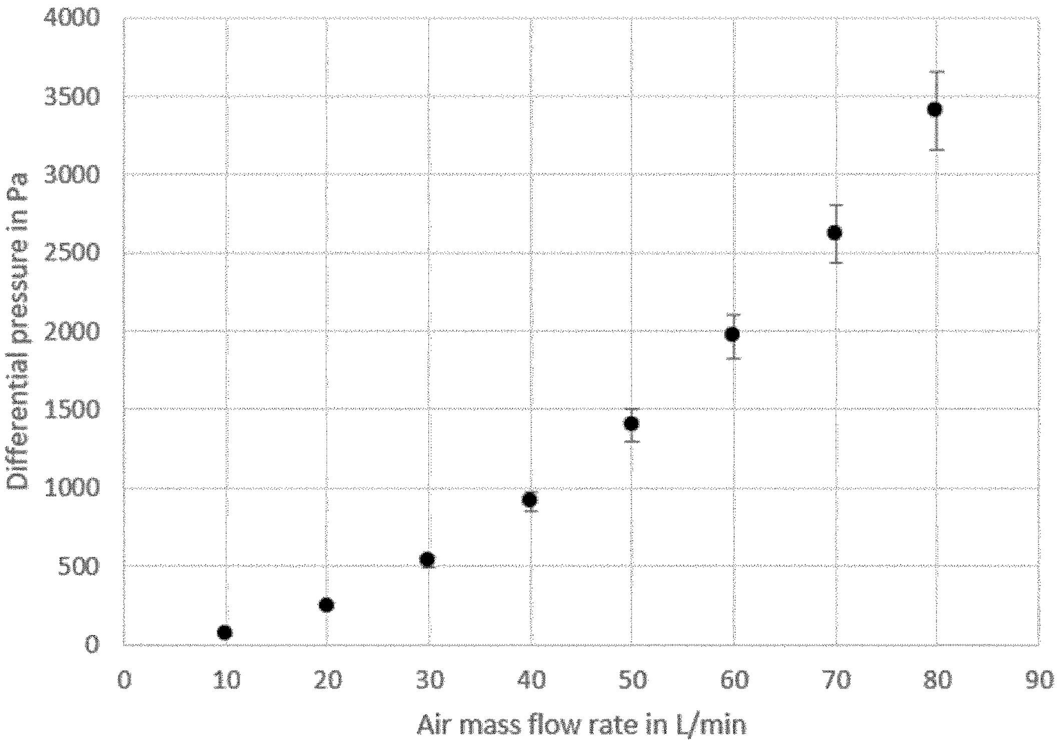
FIG. 17 shows average pressure drops from 10 sampling devices at different air mass flow rates.

FIG. 17 shows average pressure drops from 10 sampling devices and 95% confidence intervals at different air mass flow rates. The average differential pressure (or breathing resistance) of the sampling device at 40 l/min was below 1000 Pa. The average differential pressure of the sampling device at 50 l/min was below 1500 Pa. The average differential pressure of the sampling device at 60 l/min was below 2000 Pa. This breathing resistance is sufficiently low to collect exhaled breath without exposing the patient to stress.

Example 6—Deposition of Control DNA in the Dissolvable Polymer Membrane

Control DNA (and potentially other reagents) may be incorporated into the dissolvable membrane. The control DNA may then be detected in the subsequent multiplex PCR to ensure that everything worked as expected.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations within the disclosure of the present application. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A sampling device for the collection of aerosol particles contained in a breath sample of a human or animal for the purpose of sampling a non-volatile respiratory pathogen present in the breath sample, the sampling device comprising:

a housing having a flow inlet for the inflow of a breath sample into the housing and a flow outlet for the outflow of the breath sample out of the housing, the flow of the breath sample from the flow inlet to the flow outlet defining a flow path of the breath sample;

a polymer membrane arranged inside the housing, between the flow inlet and the flow outlet, and in the flow path of the breath sample, the polymer membrane configured to collect aerosol particles contained in the breath sample; and an engagement means configured for releasably engaging an elution device to the housing such that an aqueous solution introduced into the housing from the elution device elutes the aerosol particles from the polymer membrane upon contact with the aqueous solution;

wherein:

the engagement means is configured such that a laboratory tube is releasably connectable to the housing; and the laboratory tube contains the aqueous solution that is normally used in preparation for an assay selected from the group consisting of a nucleic acid amplification test (NAAT), a PCR assay, an isothermal amplification assay, a DNA hybridization assay, a CRISPR-based assay, a sequencing assay, and an immunoassay.

2. The sampling device of claim 1, wherein the polymer membrane is dissolvable in the aqueous solution.

3. The sampling device of claim 1, wherein the engagement means includes a screw thread.

4. The sampling device of claim 1, further comprising:

an accelerator arranged inside the housing, upstream of the polymer membrane;

wherein the accelerator is a nozzle arrangement having a plurality of nozzles, each nozzle defining a nozzle opening;

the nozzle arrangement extending into the flow path of the breath sample through the housing, and sized such that all of the breath sample flowing through the flow inlet of the housing flows through the nozzle arrangement; and wherein a sum of the area of all nozzle openings in the accelerator is in a range between 20 square millimeters to 65 square millimeters.

5. The sampling device of claim 1, wherein the polymer membrane has a thickness in a range between 0.5 μm to 50 μm.

6. The sampling device of claim 5, wherein the polymer membrane comprises a polymer film selected from the group consisting of polyvinyl alcohol (PVA), chitosan, polyethylene oxide (PEO), pullulan, polyvinylpyrrolidone (PVP), polyvinyl acrylic acid (PVAc), poly methacrylic acid (PMAc), hydroxypropyl methylcellulose phthalate (HPMCP), and combinations thereof.

7. The sampling device of claim 1, wherein:

the polymer membrane comprises fibers; and the fibers each have a diameter in the range between 20 nm to 1 μm.

8. The sampling device of claim 7, wherein the fibers are selected from the group consisting of polyvinyl alcohol (PVA), chitosan, polyethylene oxide (PEO), pullulan, polyvinylpyrrolidone (PVP), polyamide (PA), polyvinyl acrylic acid (PVAc), poly methacrylic acid (PMAc), hydroxypropyl methylcellulose phthalate (HPMCP), and combinations thereof.

9. The sampling device of claim 7, wherein the polymer membrane further comprises a polymer support mesh having a thickness in a range between 40 μm to 500 μm to support the fibers.

10. The sampling device of claim 1, wherein:

the polymer membrane contains assay reagents selected from the group consisting of control nucleic acid, primers, probes, nucleotides, enzymes, salts, ligand functionalized beads, and combinations thereof;

wherein the ligand functionalized beads are selected from the group consisting of magnetic beads, fluorescent nanospheres, and gold nanoparticles; and wherein the ligand is selected from the group consisting of antibodies, lipoarabinomannan binders, aptamers, peptides, and mannose binding lectins.

11. The sampling device of claim 1, wherein the sampling device is configured as a hand-held sampling device for the collection of aerosol particles present in a human breath bioaerosol.

12. A system for the collection and elution of aerosol particles contained in a breath sample of a human or animal for the purpose of sampling a non-volatile respiratory pathogen present in the breath sample, the system comprising:

a sampling device according to claim 1; and an elution device releasably connected to the housing by the engagement means;

the elution device configured for introducing the aqueous solution into the housing such that aerosol particles are eluted from the polymer membrane upon contact with the aqueous solution, and upon elution of the polymer membrane, for receiving the eluate.

13. The system of claim 12, wherein:

the elution device is a tube having a closed end and an open end opposite the closed end; and an external thread is provided at the open end of the elution device which is engageable with an internal thread of the housing of the sampling device.

14. A sampling device for the collection of aerosol particles contained in a breath sample of a human or animal for the purpose of sampling a non-volatile respiratory pathogen present in the breath sample, the sampling device comprising:

a housing having a flow inlet for the inflow of a breath sample into the housing and a flow outlet for the outflow of the breath sample out of the housing, the flow of the breath sample from the flow inlet to the flow outlet defining a flow path of the breath sample;

a polymer membrane arranged inside the housing, between the flow inlet and the flow outlet, and in the flow path of the breath sample, the polymer membrane configured to collect aerosol particles contained in the breath sample; and an engagement means configured for releasably engaging an elution device to the housing such that an aqueous solution introduced into the housing from the elution device elutes the aerosol particles from the polymer membrane upon contact with the aqueous solution;

wherein:

the polymer membrane is configured to be stable during breath sample exposure; and dissolution of the polymer membrane in the aqueous solution is triggered by a change in pH-value.

15. A method for collecting, eluting, and detecting a non-volatile respiratory pathogen present in a breath sample of a human or animal, the method comprising:

a) creating a flow of a breath sample of a human or animal through a flow inlet of a sampling device;

b) sorbing of aerosol particles contained in the breath sample with a polymer membrane arranged inside the sampling device;

c) connecting the sampling device to an elution device that contains an aqueous solution;

d) eluting the polymer membrane by bringing the aqueous solution into contact with the polymer membrane; and e) detecting a pathogen in an assay of the eluate;

wherein:

the polymer membrane is configured to be stable during breath sample exposure, and dissolution of the polymer membrane in the aqueous solution is triggered by a change in pH-value.

16. The method of claim 15, further comprising:

turning the sampling device, together with the elution device, upside down between step c) and step d).

17. The method of claim 15, wherein the assay for detecting the pathogen is an assay selected from the group consisting of a nucleic acid amplification test (NAAT), a PCR assay, an isothermal amplification assay, a DNA hybridization assay, a CRISPR-based assay, a sequencing assay, and an immunoassay.

18. The method of claim 15, wherein the sampling device comprises:

a housing having a flow inlet for the inflow of a breath sample into the housing and a flow outlet for the outflow of the breath sample out of the housing, the flow of the breath sample from the flow inlet to the flow outlet defining a flow path of the breath sample;

a polymer membrane arranged inside the housing, between the flow inlet and the flow outlet, and in the flow path of the breath sample, the polymer membrane configured to collect aerosol particles contained in the breath sample; and an engagement means configured for releasably engaging an elution device to the housing such that the aqueous solution introduced into the housing from the elution device elutes the aerosol particles from the polymer membrane upon contact with the aqueous solution.

* * * * *